United States Patent
Whitton

(10) Patent No.: US 9,562,244 B2
(45) Date of Patent: Feb. 7, 2017

(54) METHOD OF PRODUCING PLANT SUSPENSION CELLS IN A GROWTH MEDIUM ENRICHED WITH CARBONIC ACID

(75) Inventor: Peter Andrew Whitton, Nottingham (GB)

(73) Assignee: NATURALLY SCIENTIFIC TECHNOLOGIES LIMITED, Beaconsfield (GB)

( * ) Notice: Subject to any disclaimer, the term of this patent is extended or adjusted under 35 U.S.C. 154(b) by 389 days.

(21) Appl. No.: 14/118,383

(22) PCT Filed: May 18, 2012

(86) PCT No.: PCT/GB2012/051135
§ 371 (c)(1),
(2), (4) Date: Mar. 24, 2014

(87) PCT Pub. No.: WO2012/160360
PCT Pub. Date: Nov. 29, 2012

(65) Prior Publication Data
US 2014/0287458 A1  Sep. 25, 2014

Related U.S. Application Data

(60) Provisional application No. 61/509,272, filed on Jul. 19, 2011, provisional application No. 61/579,310, filed on Dec. 22, 2011.

(30) Foreign Application Priority Data

May 20, 2011 (GB) .................................. 1108519.8

(51) Int. Cl.
*A01H 4/00* (2006.01)
*C12M 3/00* (2006.01)
(Continued)

(52) U.S. Cl.
CPC .............. *C12P 7/6409* (2013.01); *A01C 3/023* (2013.01); *A01H 4/001* (2013.01); *C12M 1/002* (2013.01);
(Continued)

(58) Field of Classification Search
CPC ....... C12N 5/04; C12N 5/0018; C12N 5/8245; C12N 5/8246; C12N 5/8261; C12N 15/8241; C12N 15/8245; C12N 15/8246; C12N 15/8269; C12N 15/8286; C12N 2500/34; C12N 1/12; C12M 21/02; C12P 7/64; C12P 7/6463; C12P 7/6409; C12P 19/02; A61K 2300/00; A61K 2039/505; C07K 2317/14; A01H 1/02; A01H 4/00; A01H 3/00
See application file for complete search history.

(56) References Cited

U.S. PATENT DOCUMENTS

| 6,740,526 B1 | 5/2004 | Curtis |
| 2005/0221456 A1* | 10/2005 | Srinivasan et al. ........... 435/123 |
| 2009/0155864 A1* | 6/2009 | Bauer .................... C12M 21/02 435/134 |

FOREIGN PATENT DOCUMENTS

| DE | 100 59 372 | 6/2002 |
| EP | 2311970 | 4/2011 |

(Continued)

OTHER PUBLICATIONS

Dissertation of Yao-ming Huang, Photobioreactor Cultivation of the Cell and Tissue Cultures Derived from Marine Red Macroalga *Agardhiella subulata*. Oregon State University 2001. p. 28 in particular.*

(Continued)

*Primary Examiner* — Anne Grunberg
(74) *Attorney, Agent, or Firm* — Parker Highlander PLLC

(57) ABSTRACT

The present invention provides a method of producing a photosynthetic product, the method comprising maintaining (Continued)

a photosynthetic plant or algal cell suspension culture, in the presence of water, light and a carbonic acid-enriched growth medium. The carbonic acid may, for example be provided by feeding the photosynthetic plant cell suspension culture with a carbonic acid solution, a solid or liquid precursor thereof, or a gaseous mixture of carbon dioxide and one or more other gases. The invention also provides a method for producing a photosynthetic product, the method comprising maintaining a photosynthetic plant or algal cell suspension culture, in the presence of water, light and a carbon source selected from carbon dioxide and carbonic acid, wherein the culture is maintained at a pH of less than 7.0, preferably 4.5 to 5.5.

46 Claims, 1 Drawing Sheet

(51) Int. Cl.
    *C12P 7/64*     (2006.01)
    *C12M 3/02*     (2006.01)
    *C12M 1/00*     (2006.01)
    *A01C 3/02*     (2006.01)
    *C12P 7/06*     (2006.01)
    *C12P 19/02*     (2006.01)
    *C12P 19/12*     (2006.01)
    *C12N 1/12*     (2006.01)
    *C12R 1/89*     (2006.01)
    *C12R 1/91*     (2006.01)
    *C12N 5/04*     (2006.01)

(52) U.S. Cl.
    CPC ............... *C12M 3/02* (2013.01); *C12M 21/02* (2013.01); *C12N 1/12* (2013.01); *C12N 5/04* (2013.01); *C12P 7/06* (2013.01); *C12P 7/64* (2013.01); *C12P 19/02* (2013.01); *C12P 19/12* (2013.01); *C12R 1/89* (2013.01); *C12R 1/91* (2013.01); *Y02E 50/17* (2013.01)

(56) References Cited

FOREIGN PATENT DOCUMENTS

| JP | 55 018449 | 2/1980 |
|---|---|---|
| JP | 5 015363 | 1/1993 |
| JP | 7 087958 | 4/1995 |
| JP | 11 276157 | 10/1999 |
| WO | WO 2006/100667 | 9/2006 |
| WO | WO 2009/133351 | 11/2009 |

OTHER PUBLICATIONS https://ay14-15.moodle.wisc.edu/prod/pluginfile.php/172623/mod_resource/content/5/Carbonate%20System%20Chemistry.pdf, p. 144, section 9.5, unknown publication date.*
Wijanarko et al, Biomass Production Chlorella vulgaris Buitenzorg Using Series of Bubble Column Photo Bioreactor with a Periodic Illumination, Makara, Teknologi, vol. 12, No. 1, Apr. 2008: 27-30.*
Shiraiwa and Miyachi, Form of Inorganic Carbon Utilized for Photosynthesis Across the Chloroplast Membrane, vol. 95, No. 2, 1978, Elsevier/North-Holland Biomedical Press, pp. 207-210.*
Ono et al., Selection of Optimal Microalgae Species for CO2 Sequestration, The University of Arizona, pp. 1-7, unknown publication date.*
"Carbonic Acid", Wikipedia Article, downloaded from Princeton University website on Jul. 16, 2013.
Alberts et al. *Molecular Biology of the Cell*, $2^{nd}$ Ed. New York: Garland Publishing, 1989. 368-369. Print.
Chen et al., "Plant nitrogen acquisition and interactions under elevated carbon dioxide: impact of endophytes and mycorrhizae", *Global Change Biology*, 13:1238-1249, 2007.
Chinnasamy et al., "Biomass production potential of wastewater alga *Chlorella vulgaris* ARC 1 under elevated levels of $CO_2$ and temperataure", *International Journal of Molecular Sciences*, 10(2):518-532, 2009.
Emerson and Green, "Effect of hydrogen-ion concentration on *Chlorella* photosynthesis", *Plant Physiology*, 13(1):157-68, 1938.
Fischer et al., "Cultivation of photoautotrophic plant cell suspensions in the bioreactor: influence of culture conditions", *Journal of Biotechnology*, 41(1):19-28, 1995.
Greenwood and Earnshaw. *Chemistry of the Elements*. Oxford: Pergamon, 1984, 329. Print.
Ho and Sturtevant, "The kinetics of the hydration of carbon dioxide at 25°", *The Journal of Biological Chemistry*, 238(10):3499-3501, 1963.
Kim et al., "Relationship of viability and apoptosis to taxol production in *Taxus* sp. suspension cultures elicited with methyl jasmonate", *Biotecnol. Prog.*, 21:700-707, 2005.
Malińska and Zabochnicka-Świątek. "Biosystems for air protection", *Air Pollution*. Villanyi (Ed.), InTech, 2010. 177-193. Online.
Mathews and van Holde. *Biochemistry*. Redwood City: Benjamin/Cummings, 1990. 660-661. Print.
Meyer et al., "Oxidized phytosterols increase by ageing in photoautotrophic cell cultures on *Chenopodium rubrum*", *Phytochemistry*, 45(2):297-302, 1997.
PCT International Preliminary Report on Patentability issued in International Application No. PCT/GB2012/051135, mailed Sep. 19, 2013.
PCT International Search Report and Written Opinion issued in International Application No. PCT/GB2012/051135, mailed Dec. 19, 2012.
Putt et al., "An efficient system for carbonation of high-rate algae pond water to enhance $CO_2$ mass transfer", *BioResource Technology*, 102(3):3240-3245, 2011.
Roa & De Kok, *Phyton.*, 34(2), 279-290, 1994.
Rodriguez-Maroto et al., "Air bubbling results in carbon loss during macroalgal cultivation in bicarbonate-enriched media: experimental data and process modeling", *Aquacultural Engineering*, 32(3-4):493-508, 2005.
Roeske et al., "Photosynthetic carbon metabolism in photoautotrophic cell suspension cultures grown at low and high $CO_2$", *Plant Pysiol.*, 91:1512-1519, 1989.
Roitsch and Sinha, "Application of photoautotrophic suspension cultures in plant science", *Photosynthetica*, 40(4):481-492, 2002.
Sajc et al., "Bioreactors for plant engineering: an outlook for further research", *Biochemical Engineering Journal*, 4:89-99, 2000.
Search Report issued in United Kingdom Application No. GB1108519.8, mailed Sep. 20, 2011.

* cited by examiner

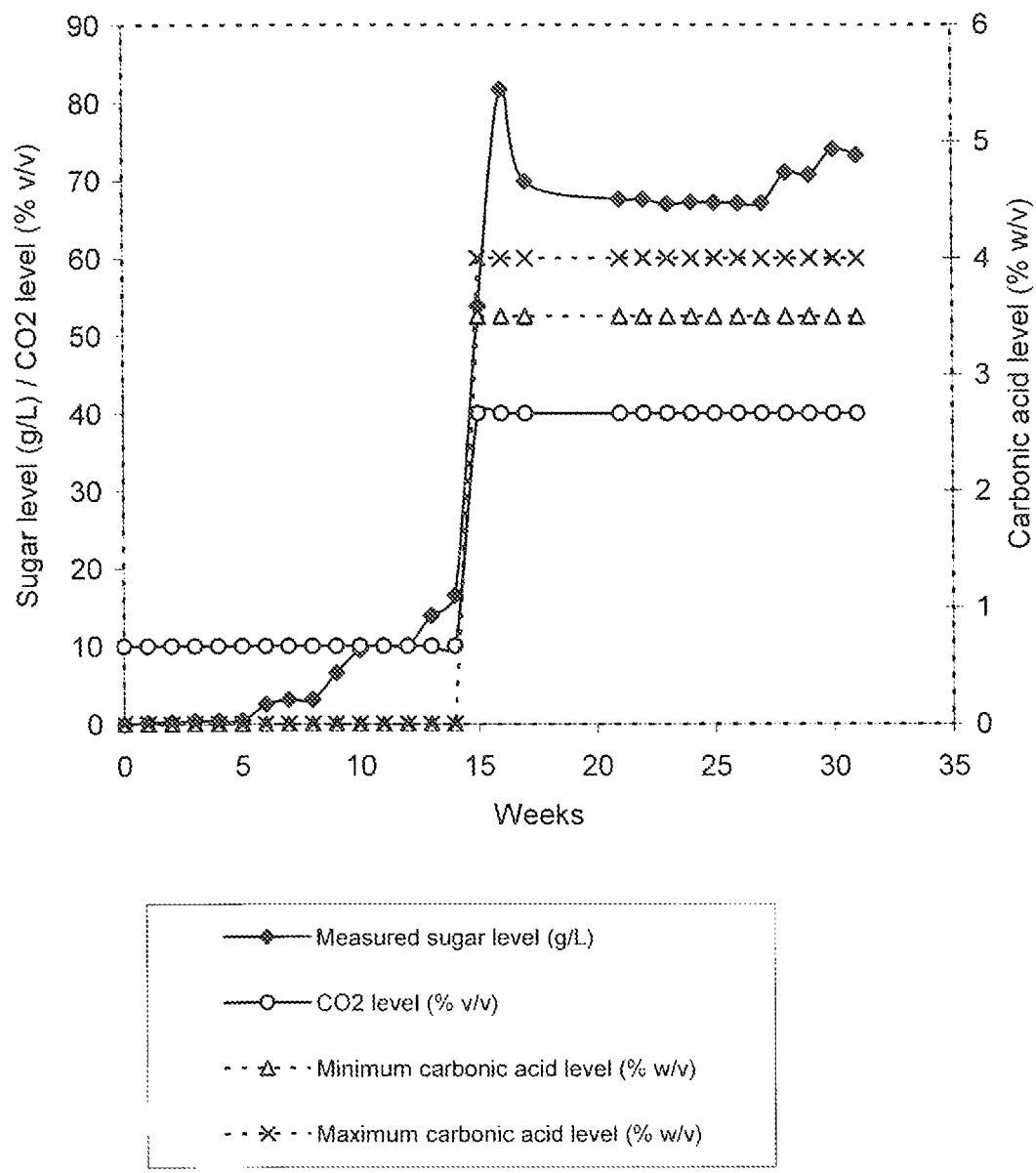

METHOD OF PRODUCING PLANT SUSPENSION CELLS IN A GROWTH MEDIUM ENRICHED WITH CARBONIC ACID

This application is a national phase application under 35 U.S.C. §371 of International Application No. PCT/GB2012/051135, filed May 18, 2012, which claims priority to Great Britain Application No. 1108519.8, filed May 20, 2011, U.S. Provisional Application No. 61/509,272, filed Jul. 19, 2011, and U.S. Provisional Application No. 61/579,310, filed Dec. 22, 2011. The entire text of each of the above referenced disclosures is specifically incorporated herein by reference.

FIELD OF THE INVENTION

The invention relates to a highly efficient process for the photosynthetic production of products (for example sugar, typically mono- and/or di-saccharides, for example glucose, sucrose, and/or fructose; glyceraldehyde; glycerose; and/or one or more starches) by photosynthetic plant and/or algal cell suspension cultures that requires a substantially reduced input of energy (primarily in the form of light) compared to conventional photosynthetic processes.

INTRODUCTION

The listing or discussion of an apparently prior-published document in this specification should not necessarily be taken as an acknowledgement that the document is part of the state of the art or is common general knowledge.

The production of oil from seed crops dominated the plant oil industry for many years, whereas the use of algae to produce oils has also been previously proposed.

The present Applicant has recently described a totally different approach to the production of plant oils, as discussed in International Patent Application No. PCT/GB2009/001066 (published as WO 2009/133351), the contents of which are incorporated herein in their entirety by reference. Instead of a seed crop in soil, WO 2009/133351 describes the suspension culture of selected oil producing cells (such as mesophyll cells) which are used to express oil into the media. This differed greatly from previous disclosures of using algae, which require significant energy for the solvent recovery of oils, after some form of cell lysis, both of which consume over 20% of the energy produced by the oil. In the process described in WO 2009/133351, oil is generated from sugars and starches preferably produced using a unique photobioreactor system which enables higher plant cells to generate the food sources needed for the oil production step. Furthermore, significant efforts were made to derive a custom, unique and highly efficient nutrient composition, optimized for each of the two basic steps. To protect against contamination and to fight such infections when they occur, an additional innovation was the use of in situ antifungals and antibiotics which were found in nature in higher plants to keep infections from taking over the plant.

Accordingly, the process described in WO 2009/133351 eliminates the requirement of algae-derived oil for solvent extraction and distillation. The process of WO 2009/133351 is thus far more "green" in terms of an oil production facility given it uses carbon dioxide, water and a light source. This is a simple and measurable and provable but elegant process wherein oil is removed from the top layer in the tank every day and measuring it compared to the volume of liquid sugars and their compositional analyses.

By contrast, in algae, using sugars for heterotrophic growth, a typical maximum range as published by Wu et al (Chapter 17, Production of Biodiesel, from algal biomass: current perspectives and future, Biofuels, 2011, pg 399-413), is 0.32 lbs of oil produced for each pound of sugar added in the form of glucose.

Once cells have achieved optimal concentrations, the process described in WO 2009/133351 shows a rate of 1,200 liters of oil in a 50,000 liter reactor (44,000 liter working volume) using a daily rate of sugar liquids of 2,160 liters, carried in 4320 liters of enriched media at a density of 500 g/liter. The overall mass efficiency is 0.55 lbs of oil per pound of sugar, significantly higher than algae.

In addition, the electrical power requirements for the plant cell culture process described in WO 2009/133351 is significantly lower given the air volumes are substantially lower due to high efficiency rates of the sugar to oil conversion. It may also be possible to use this second step to enrich air to produce oxygen which can be further purified using membrane technologies.

The Applicant has now focused on further developing the first step of the process described in WO 2009/133351, which is the photosynthetic manufacture of sugars by a photosynthetic cell suspension culture. As discussed in more detail below, the Applicant has unexpectedly determined that photosynthetic plant and algal cell suspension cultures are capable of a substantially more efficient form of photosynthesis when carbonic acid is provided as the substrate for photosynthesis instead of gaseous carbon dioxide, thereby requiring lower energy input in order to produce photosynthetic products.

Gaseous $CO_2$ will dissolve into the growth medium, and dissolved $CO_2$ is in equilibrium with carbonic acid in the growth medium. However, the extent to which gaseous $CO_2$ dissolves into a growth medium and forms carbonic acid can depend on a number of factors, including the concentration of the $CO_2$ in the gas, the size of bubbles of $CO_2$-containing gas introduced into the growth medium, the bubble transit period and/or path length through the growth medium, and the pressures of both the growth medium through which the bubbles pass, and of the $CO_2$-containing gas that is introduced into the medium. Moreover, even when formed, carbonic acid can break down to release gaseous carbon dioxide and water, and this process occurs more quickly at lower pressures, which may be typical in shallow cultures. When the skilled person has in mind a particular level of carbonic acid to generate or maintain, in accordance with disclosure of the present invention, then (in one embodiment of the invention) it is a matter of routine to achieve this by feeding the growth medium with $CO_2$-containing gas of suitable $CO_2$ concentration, with a suitable bubble size, suitable bubble transit period and/or path length, and at suitable pressures in order to achieve and/or maintain the desired level of carbonic acid. However, if inappropriate parameters are used, then a desired level of carbonic acid will not follow. Accordingly, therefore, prior art disclosures of bubbling of carbon dioxide gas into culture media, without an indication of the $CO_2$ concentration, bubble size, transit time/path length, and pressure, even when highly concentrated levels of $CO_2$ are used, cannot be assumed to achieve or maintain any particular level of carbonic acid in the growth medium.

The Applicant is not aware of any previous reports that would have lead the skilled person to focus on providing carbonic acid in an adequate amount for a plant or algal cell suspension culture to use it as the substrate for photosynthesis, instead of using gaseous carbon dioxide.

WO 2009/133351 describes the use of a plant cell suspension culture of photosynthetic plant cells. It reports on the use of suspension cultures of photosynthetic plant cells to produce their own sugars from light, water and gaseous carbon dioxide ($CO_2$), via the photosynthetic process, such that sugars are produced to use as an energy source for the growth of the oil-producing plant cells and as a substrate for their production of fatty acids and/or oils, or as a sugar source for use by any process that utilises sugars, such as any culture of biological material. In Example 5 of WO 2009/133351 it is suggested that the cell suspension culture of photosynthetic cells may be grown in the culture medium using an air stream of about 3660 liters per minute for a 20,000 liter tank at a $CO_2$ density of about 10% (i.e. a 10% $CO_2$/air mixture). However, there is no consideration in WO 2009/133351 of the use of carbonic acid as a carbon source for photosynthesis, and no teaching that would lead the skilled person to form or maintain carbonic acid at any particular level in the growth medium.

JP 05-015363 describes a method of tissue culture of plants aimed at increasing the rate of plant growth. This is not, however, a method for plant cell suspension culture. Rather it describes a method for the culture of plant material having organised tissue structure, including tissue culture (paras [0002] and [0005]), and the culture of whole plants (para [0013]) in which transpiration and nutrient uptake are promoted and the vitrification of stems and leaves is suppressed (para [0012]). Moreover, JP 05-015363 does not teach or suggest that its method can be used to produce or recover photosynthetic products such as sugars. The objective is to enhance the growth rate of the culture plant or plant tissues (para [0011]). It describes the tissue culture of plant material in sugar-free liquid culture media. The media is sugar-free to reduce pathogen growth. Its method involves supplying a "high-concentration carbon dioxide to the liquid culture medium under intense light" (paragraph [0006]). The "high" level of carbon dioxide in the supplied gas of JP 05-015363 is said to be 1000-2000 ppm in air (para [0010]). This equates to only 0.1 to 0.2% of $CO_2$ by volume. JP 05-015363 teaches that the carbon dioxide-enriched (i.e. 0.1-0.2%) air is pumped into the liquid culture medium through an aeration device fitted at the bottom of the culture tank, and released in the form of "fine" bubbles (Para [0011]). However, there is no specific consideration given in JP 05-015363 to $CO_2$ bubble size, the time in which the bubble is in transit through the culture medium and the pressure under which the culture is maintained in a manner that allows the reader to determine the extent to which gaseous $CO_2$ could become dissolved in the medium and converted to carbonic acid. Nor is any consideration given to whether the carbon dioxide dissolves in the culture medium to form carbonic acid to any particular level. Accordingly, there is no reproducible teaching in JP 05-015363 that would lead the user to achieve or maintain any particular level of carbonic acid in the growth medium.

Previously, both phototrophic and heterotrophic algae cultivation has been used to generate lipids which, with suitable extraction processes, can also produce oils. Algae however, produces a broad spectrum of compounds which vary amongst species as well as within a given cultivar based on growth and nutrient conditions which are difficult to replicate.

Those using heterotrophic algae require large amounts of low cost sugars. The fermentation reactors also have high aeration demands, commonly requiring a high volume up to 0.5 $V_{air}/V_{reactor}$ per minute, which consumes significant electrical power to drive air compressors, spargers and high speed mixers.

Those using phototrophic algae typically culture in algae ponds using gas spargers to introduce gaseous carbon dioxide, but the equilibrium concentration is quite low and absorption is limited by a column or pond depth of only 15 to 20 cm, making the carbon dioxide absorption process highly inefficient and partial pressures of carbon dioxide far below desirable levels.

JP 07-087958 reports that blue-green algae in soil is considered to be a composite of bacteria and micro-algae and it proposes a method for the isolation of the microalgae separately from the bacterial component. After isolation of the microalgae, a culture method is proposed, involving "high" $CO_2$, "low" pH (a pH close to 4 is mentioned) and light at low intensity of 10~50 μ-Einsteins/m²/sec. FIG. 2 shows that 10% $CO_2$ led to enhanced propagation of algae compared to both 0.03% and 20% $CO_2$ levels. This clearly indicates that higher $CO_2$ levels, such as around 20%, were not favoured in the prior art for the culture of at least certain types of algae.

Moreover, there are no teachings in JP 07-087958 that allows the reader to determine the extent to which gaseous $CO_2$ became dissolved in the medium and, if at all, converted to carbonic acid. Certainly, there are no reproducible teachings in JP 07-087958 that would lead the skilled person to culture the microalgae with any particular level of carbonic acid in the growth medium.

JP 11-276157 relates to a culture method of microalga belonging to the genus *Coccomyxa*, which is taught to grow autotrophically by photosynthesis with carbon dioxide as a carbon source (para [0001]) provided from air, waste gas, or the like (para [0005]). The operational range of gaseous $CO_2$ concentration used for growth is said to be 0.03% to 40%, whereas 0.03% to only 5% is said to be optimum (claim 2 and para [0017]). Thus, like JP 07-087958, it is also suggested in JP 11-276157 that higher $CO_2$ levels, such as greater than 5%, are not favoured for the culture of at least certain types of algae.

Again, there are no teachings in JP 11-276157 that allows the reader to determine the extent to which gaseous $CO_2$ became dissolved in the medium and, if at all, converted to carbonic acid. Certainly, there are no reproducible teachings in JP 11-276157 that would lead the user to culture the microalgae with any particular level of carbonic acid in the growth medium.

Another strategy for algal culture growth and producing cell biomass is described in WO 2006/100667, in which Examples 1 and 2 report that $CO_2$ gas from the combustion of natural gas can be captured and concentrated as sodium bicarbonate or ammonium bicarbonate. The solutions of sodium bicarbonate can be heated to produce a gas stream containing greater than 80% $CO_2$; whereas $CO_2$ may be liberated from ammonium bicarbonate in the presence of nitric acid to produce a gaseous stream of greater than 90% $CO_2$ at super-atmospheric pressure. WO 2006/100667 teaches that these gaseous streams can be introduced into a photosynthetic bioreactor containing micro-algae and nutrients in the presence of sunlight, and the $CO_2$ is consumed and algal biomass increases, followed by recovery of the biomass. However, there is no experimental evidence in WO 2006/100667 to show that algae tolerated these high levels of $CO_2$, much less that they led to greater productivity than lower $CO_2$ levels, such as the 10% level that was proven to be preferred in JP 07-087958.

In any case, WO 2006/100667 does not further consider the manner in which $CO_2$ is provided to the culture. There are no teachings of, for example, $CO_2$ bubble size, the time in which the bubble is in transit through the culture medium and the pressure under which the culture is maintained, in a manner that allows the reader to determine the extent to which gaseous $CO_2$ could become dissolved in the medium and, if at all, converted to carbonic acid, nor the extent to which any carbonic acid in the culture medium would be stably maintained. Accordingly, there are no reproducible teachings in WO 2006/100667 that would lead the user to culture the microalgae with any particular level of carbonic acid in the growth medium.

In recent discoveries, instead of introducing gaseous carbon dioxide directly, several groups have suggested the use of algal species that can tolerate sodium bicarbonate, and that the chemical introduction of this species increases growth rate and/or rate of oil formation by the algae.

For example, US 2009/0155864 suggested the use of sodium carbonate or bicarbonate, or potassium carbonate or bicarbonate, as a stable form in which to capture gaseous $CO_2$ (like WO 2006/100667), and then further suggested the use of the captured form to transport carbon dioxide from its source, to a photo-bioreactor (containing a recombinant photosynthetic organism, e.g. photosynthetic algae). US 2009/0155864 teaches the addition of the carbonate or bicarbonate to a photo-bioreactor containing both acid and the enzyme carbonic anhydrase. The acid (for example, producing a pH of 6) causes the conversion of the carbonate or bicarbonate to carbonic acid, and "nearly all" of the carbonic acid is immediately converted to gaseous $CO_2$ due to the presence of the enzyme carbonic anhydrase. The $CO_2$ gas is taught to serve as a carbon source for recombinant photosynthetic organism growth.

Since the system used in US 2009/0155864 converts carbonate or bicarbonate to carbonic acid in the presence of the enzyme carbonic anhydrase, and since that enzyme immediately converts carbonic acid to $CO_2$ gas, then the levels of carbonic acid in the photo-bioreactor described in US 2009/0155864 remain low, since any carbonic acid that is created is unstable, and is rapidly converted to $CO_2$ gas. Moreover, any liberated $CO_2$ gas that did then dissolve in the growth medium and convert to carbonic acid would be immediately converted to gaseous $CO_2$ again by the action of the enzyme carbonic anhydrase. Accordingly, the teaching of US 2009/0155864 would lead the skilled person to produce a culture with effectively very low, or even no, carbonic acid present therein.

DESCRIPTION OF THE INVENTION

In contrast to the prior art, as mentioned above, the Applicant has unexpectedly determined that photosynthetic plant and algal cell suspension cultures are capable of a substantially more efficient form of photosynthesis when carbonic acid is provided as the substrate for photosynthesis instead of gaseous carbon dioxide, thereby requiring lower energy input in order to produce photosynthetic products.

Accordingly, a first aspect of the present invention provides a method of producing a photosynthetic product, the method comprising the step of maintaining a photosynthetic plant or algal cell suspension culture, in the presence of water, light and a carbonic acid-enriched growth medium.

Any photosynthetic product may be produced, although in one embodiment the photosynthetic product may, for example, be (or comprise) a sugar that is produced by the photosynthetic process, such as mono- and/or di-saccharides (for example glucose, sucrose, and/or fructose), glyceraldehyde, glycerose, and/or one or more starches.

In one embodiment, the concentration of carbonic acid in the carbonic acid-enriched growth medium is at least about 0.1% w/v (that is, weight of carbonic acid (kg) per volume of growth medium (L)), preferably at least 0.2% w/v, 0.3% w/v, 0.4% w/v, 0.5% w/v, 0.6% w/v, 0.7% w/v, 0.8% w/v, 0.9% w/v, 1.0% w/v, 1.5% w/v, 2.0% w/v, 2.5% w/v, 3.0% w/v, 3.5% w/v, 4.0% w/v, 5.0% w/v, 6.0% w/v, 7.0% w/v, 8.0% w/v, 9.0% w/v or more such as up to about 10.0% w/v. Thus, one preferred range may be of from about 0.1% w/v to about 10% w/v carbonic acid in the growth medium, for example of from about 0.5% w/v to about 10% w/v, of from about 1.0% w/v to about 10% w/v, of from about 5% w/v to about 10% w/v, and so on. Values higher than 10% w/v are also contemplated, up to saturated levels of carbonic acid.

In this context, "about" can be construed as encompassing values that are ±50%, 40%, 30%, 20%, 10%, 5%, 4%, 3%, 2%, or 1% of the stated value. For example, therefore, the value of "about 4% v/w" can include the meaning "4% w/v±50% of the stated value" which equates to the range of from 2% w/v to 6% w/v.

It is noted that carbonic acid has the formula $H_2CO_3$, and a molecular mass of 62.03 g/mol. Therefore, a concentration of, for example, 4% w/v is the same as 40 g carbonic acid per L of growth medium, which in turn corresponds to 40/60.2=0.664 mol/L, i.e. carbonic acid at 4% w/v corresponds to a carbonic acid concentration of 0.664M.

The amount or concentration of carbonic acid present in a growth medium can be determined by any suitable method known in the art. For example, in one embodiment, the amount or concentration of carbonic acid present in a growth medium may be determined by a method comprising the steps of—

(a) taking an aliquot of growth medium of defined volume;
(b) adding excess carbonic anhydrase enzyme in order to covert any carbonic acid present in a growth medium into gaseous carbon dioxide,
(c) capturing the gaseous carbon dioxide that is released and measuring its volume.

The skilled person can calculate the number of moles of carbon dioxide released from the aliquot, from the measurement of the volume of carbon dioxide that is captured. For example, at standard temperature and pressure, 1 mole of an ideal gas has a volume of 22.4 L (and $CO_2$ closely conforms to an ideal gas). From there, the skilled person can determine how many moles of carbonic acid were converted to $CO_2$ and released from the aliquot, and thereby determine the starting amount and concentration of carbonic acid in the aliquot of growth medium.

In a further embodiment, the method of the first aspect of the present invention includes the step of maintaining the level of carbonic acid in the carbonic acid-enriched growth medium at a steady level.

In one preferred embodiment, a level of carbonic acid in the carbonic acid-enriched growth medium can be said to be maintained at a steady level if the level is maintained for a period for time, for example, for at least 1 hour, 2 hours, 4 hours, 8 hours, 12 hours, 24 hours, 2 days, 5 days, 1 week, 2 weeks, 3 weeks, 4 weeks, 5 weeks, 6 weeks, 7 weeks, 8 weeks, 9 weeks, 10 weeks, 15 weeks, 20 weeks, 35 weeks, 30 weeks, 35 weeks, 40 weeks, 45 weeks, 50 weeks, or more. In this context, the level of carbonic acid can be said to be "maintained" if, over the selected period of time, the level is prevented from falling below at least about 0.1% w/v, preferably at least about 0.2% w/v, 0.3% w/v, 0.4% w/v, 0.5% w/v, 0.6% w/v, 0.7% w/v, 0.8% w/v, 0.9% w/v, or 1.0% w/v, and more preferably is kept at a level of or higher than at least about 1.5% w/v, 2.0% w/v, 2.5% w/v, 3.0% w/v, 3.5% w/v 4.0% w/v, 5.0% w/v, 6.0% w/v, 7.0% w/v, 8.0% w/v, 9.0% w/v or more such as up to about, typically about 10.0% w/v. It may further be preferred that the level of carbonic acid in the carbonic acid-enriched growth medium is prevented from varying by more than ±5.0% w/v, ±4.0% w/v, ±3.0% w/v, ±2.0% w/v, ±1.0% w/v, ±0.5% w/v, ±0.4% w/v, ±0.2% w/v, ±0.1% w/v, ±0.05% w/v, or less, during the selected period of time.

The growth medium may be enriched with carbonic acid and/or the level of carbonic acid may be maintained in the growth medium by introducing carbonic acid into the growth medium in an appropriate amount and at an appropriate rate, for example by feeding the photosynthetic plant cell suspension culture with one or more of:

(a) a carbonic acid solution,
(b) a solid or liquid precursor of a carbonic acid solution, or
(c) a gaseous mixture of carbon dioxide and one or more other gases, such as a mixture consisting or comprising of carbon dioxide and oxygen and optionally also nitrogen, or a mixture of atmospheric air and carbon dioxide, the gaseous mixture preferably having a carbon dioxide concentration by volume of greater than 10%, more preferably at, about, or greater than 15%, 20%, 35%, 30%, 35% or 40%, such as about 40%, for example up to about 50%, 45% or 40%. More preferably the carbon dioxide concentration is 30-45%, 35-45%, yet more preferably 40%±4, 3, 2 or 1%, most preferably 40%.

By using highly concentrated carbon dioxide in the gaseous mixture it is possible to use much lower gas volumes in order to deliver the same amount of $CO_2$, which in turn can permit smaller bubble sizes. This means longer transit times for the $CO_2$ to pass through the media, thus enhancing the opportunity for the $CO_2$ in the bubbles to be absorbed and dissolved into the growth medium and, form there, converted into carbonic acid. Also, by using more concentrated $CO_2$, there is a lower requirement to remove excess gases from the culture vessel thus allowing the use of smaller diameter pipe work which reduces capital expenditure. An additional overall effect is to reduce the amount of foam produced within the vessel as this is directly proportional to the total gas flow, thus enabling more efficient production in the tank.

To the Applicant's knowledge, there are no prior disclosures or suggestions of using such high $CO_2$ levels in plant cell suspension culture. It was thought that high levels of $CO_2$ would be toxic and therefore huge volumes of air would have to be passed through the vessel in order to deliver the required quantity of $CO_2$. Roa & De Kok 1994, *Phyton.*, 34(2), 279-290 suggests "high" $CO_2$ for growing *Triticum* plants, but the amount considered to be high is only 0.07% (abstract). Chen et al, 2007, *Global Chance Biology,* 13, 1238-1249 also discussed "elevated" $CO_2$ levels which it considers to be only 730 µmol mol$^{-1}$, that is, only 0.073%. Kim et al, 2005, *Biotecnol. Prog.* 21, 700-707 described a plant cell culture that uses 5% $CO_2$ was used. U.S. Pat. No. 6,740,526 also uses 5% $CO_2$ (see Example 7, in col. 14). Thus, the art had generally, at most, used $CO_2$ no higher than as 5% in plant cell suspension cultures and would not have considered using higher levels, since these were considered to be likely to toxic to plants first, by inhibiting respiration, and second by resulting the toxic accumulation of sugars. WO 2009/133351 described 10% carbon dioxide (Example 5). None of these documents teach or suggest that carbonic acid should be provided for photosynthesis, much less that it can be directly used instead of gaseous carbon dioxide in the photosynthetic process by the key photosynthetic enzyme Rubisco (Ribulose-1,5-bisphosphate carboxylase oxygenase).

The high levels of gaseous carbon dioxide for use in the present invention, as contemplated in option (c) above, thus increase the extent to which the carbon dioxide is dissolved in the photosynthetic cell suspension culture, and assists in the production of an enriched level of carbonic acid that can be used in the photosynthetic process.

It is preferred that the efficiency of absorption of the carbon dioxide component of the gaseous mixture (assessed by dividing the % volume $CO_2$ content of the gas introduced into the culture with the % volume $CO_2$ content of the exhaust stream, and multiplying by 100) by the photosynthetic cell suspension culture is greater than 40%, preferably greater than 50%, 60%, 70%, or 80%, more preferably about 90%, or about 95%, or more (in this context "about" refers to ±4, 3, 2 or 1%).

In addition to the concentration of the $CO_2$ in the gas that is introduced into the culture, the efficiency of $CO_2$ absorption will also directly correlate with three further factors—

The size of the bubble: the smaller the bubble the more efficient it will be, ideally the bubbles will have a mean average diameter at the point of introduction into the culture medium of about less than 1 mm, such as less than 0.5 mm, 0.4 mm, 0.3 mm, 0.2 mm. 0.1 mm, 90 µm, 80 µm, 70 µm, 60 µm, 50 µm, 40 µm, 30 µm, 20 µm, or 10 µm.

The length of time the bubble is in the culture (i.e. the transit period): the taller the culture column (i.e. the longer the path length of the bubble) the more time it takes the bubble to transit the medium and hence spends longer in the media thus enhancing the opportunity for the $CO_2$ in the bubbles to be absorbed and dissolved into the growth medium and, form there, converted into carbonic acid. Typically, the column height used in the present invention is, is up to, or is at least, about 0.5 meter, 1 meter, 1.5 meters, 1.8 meters, 2 meters, 3 meters, 4 meters or 5 meters in height (in this context the term about is used to refer to ±0.5, 0.4, 0.3, 0.2 or 0.1 meters).

The pressure of the photosynthetic cell suspension culture medium: In one embodiment, the carbonic acid is provided by feeding the gaseous mixture of atmospheric air and carbon dioxide to the photosynthetic cell suspension culture medium, wherein the photosynthetic cell suspension culture is maintained at a pressure of at least, or greater than, 1 atm, such as about greater than 1 atm to 4 atm, such as greater than any value falling within the range of ≥1 to 2 atm, preferably at a pressure of about 3 atm±0.9, 0.8, 0.7, 0.6, 0.5, 0.4, 03, 0.2, 0.1 atm, such as 3.2 atm. Increasing pressure has the benefit of increasing the solubility of the $CO_2$ that is bubbled through and also has the additional benefit of reducing the breakdown of dissolved carbonic acid to form gaseous carbon dioxide and water, and thereby can assist in maintaining the desired level of carbonic acid in the culture medium.

It is further preferred that the gaseous mixture of atmospheric air and carbon dioxide is fed to the photosynthetic cell suspension culture medium at a pressure greater than the pressure at which the photosynthetic cell suspension culture is maintained.

Preferably the partial pressure of carbon dioxide (that is, the level of $CO_2$ in the liquid phase of the cell culture medium compared to level of $CO_2$ in the gaseous phase) is greater than $10^{-8}$, preferably greater than $10^{-7}$, $10^{-6}$, $10^{-5}$, $10^{-4}$, such as within the range of about $10^{-5}$ to about $10^{-4}$.

When the skilled person has in mind a particular level of carbonic acid to generate or maintain, in accordance with foregoing disclosure of the present invention, by feeding the plant cell culture medium with a mixture of air and $CO_2$ gas, then it is a matter of routine to establish a suitable bubble size, suitable bubble transit period and/or path length, and suitable pressures in order to achieve and/or maintain the desired level of carbonic acid. This can be arrived at using routine trial and error, and numerous combinations can provide satisfactory results. For example, a suitable combination to produce a carbonic acid-enriched growth medium in accordance with the present invention may be to use a mean average diameter bubble size of 0.2 mm, a transit period of 4 seconds, a path length of 1.8 m, culture pressure 3.2 atm, where the gas bubbles that are introduced into the culture contain 40% $CO_2$ v/v. The skilled person will appreciate that a corresponding level of carbonic acid may be obtained even if one or more of these parameters is altered in a way that favours reduced formation carbonic acid, provided that one or more of the other parameters is altered in a way that favours increased formation of carbonic acid.

Even though the skilled person can readily establish suitable parameters to use when they wish to generate or maintain a particular level of carbonic acid, it is important to take all of these factors into account in order to do so when providing a culture with gaseous carbon dioxide. If the selected $CO_2$ concentration, the selected bubble size, the selected transit time/path length and/or the selected pressures are inappropriate, then enrichment of the growth medium to high levels of carbonic acid in accordance with the present invention will not follow. In those situations, for example, where the path length is too short, or the bubbles are too large, or the pressure is too low, then inadequate amounts of gaseous $CO_2$ will dissolve into the growth medium, even if the $CO_2$ concentration used is high. Dissolved $CO_2$ is in equilibrium with carbonic acid in the growth medium, so a method of providing bubbles of $CO_2$ which leads to inadequate levels of dissolution of $CO_2$ in the growth medium will also be inadequate to achieve and/or maintain the requisite levels of carbonic acid. Accordingly, therefore, prior art disclosures of the bubbling of carbon dioxide gas into culture media, without any indication of the bubble size, transit time/path length or pressure, even when highly concentrated levels of $CO_2$ are used, cannot be assumed to achieve or maintain any particular level of carbonic acid in the growth medium.

Alternatively, in option (a) (that is, where the growth medium is enriched with carbonic acid and/or the level of carbonic acid in the growth medium is maintained by introducing a carbonic acid solution into the growth medium) then preferably the volume of carbonic acid solution added the growth medium is relatively small in comparison to the total volume of the photosynthetic plant or algal cell suspension culture, such as less than 10%, 5%, 2%, 1%, 0.5%, 0.1%, 0.05% or 0.01% of the total volume of the suspension culture.

Alternatively, in the case of option (b) (that is, where the growth is enriched with carbonic acid and/or the level of carbonic acid may be maintained by introducing a solid or liquid precursor of a carbonic acid solution) a solid or liquid precursor of a carbonic acid solution may be any solid or liquid component, or mixture of components, that can be added to the photosynthetic plant or algal cell suspension culture to cause the generation of carbonic acid. For example, the addition of a bicarbonate to cell culture medium under acidic condition will cause the bicarbonate to convert to carbonic acid and gaseous carbon dioxide. As with option (a), preferably the volume of any liquid precursor added is relatively small in comparison to the total volume of the photosynthetic plant or algal cell suspension culture, such as less than 10%, 5%, 2%, 1%, 0.5%, 0.1%, 0.05% or 0.01% of the total volume of the suspension culture.

In both options (a) and (b), like option (c), the column height of the culture medium may optionally be up to about 0.5 meter, 1 meter, 2 meters, 3 meters, 4 meters or 5 meters in height (in this context the term about is used to refer to ±0.5, 0.4, 0.3, 0.2 or 0.1 meters) and/or the pressure of the photosynthetic cell suspension culture medium may be maintained at a pressure of at least, or greater than, 1 atm, such as about greater than 1 atm to 4 atm, such as greater than any value falling within the range of ±1 to 2 atm, preferably at a pressure of about 3 atm±0.9, 0.8, 0.7, 0.6, 0.5, 0.4, 0.3, 0.2, 0.1 atm. Increased pressure in the culture medium, which can (at least in part) be achieved through the use increased column height of the growth medium, has the additional benefit of reducing the breakdown of dissolved carbonic acid to form gaseous carbon dioxide and water, and thereby can assist in maintaining the desired level of carbonic acid in the culture medium.

As discussed above, US 2009/0155864 suggests the use of sodium carbonate or bicarbonate, or potassium carbonate or bicarbonate, as a stable form in which to capture and transport carbon dioxide from its source, to a photo-bioreactor (containing a recombinant photosynthetic organism, e.g. photosynthetic algae). It teaches the addition of the carbonate or bicarbonate to a photo-bioreactor. The acid (for example, producing a pH of 6) causes the conversion of the carbonate or bicarbonate to carbonic acid. However, the system discussed in US 2009/0155864 also includes the enzyme carbonic anhydrase, and "nearly all" of the carbonic acid that is produced from the carbonate or bicarbonate is immediately converted to gaseous $CO_2$ by the enzymatic action of the carbonic anhydrase. According to the teaching of US 2009/0155864, the $CO_2$ gas serves as a carbon source for recombinant photosynthetic organism growth.

Since the system used in US 2009/0155864 converts carbonate or bicarbonate to carbonic acid in the presence of the enzyme carbonic anhydrase, and since the enzyme immediately converts carbonic acid to $CO_2$ gas, the levels of carbonic acid in the photo-bioreactor described in US 2009/0155864 remain low, since any carbonic acid that is present is unstable, and is rapidly converted to $CO_2$ gas.

In contrast, the present invention relates to a method wherein the growth medium is enriched with carbonic acid, and preferably wherein the enriched level is maintained so that it can be constantly used as a carbon source by the photosynthetic cells in the culture. Accordingly, it may be particularly preferred that the growth medium used in the present invention does not contain any substantial levels of, and preferably no, added carbonic anhydrase enzyme and/or methods of the present invention specifically exclude the step of adding a carbonic anhydrase enzyme supplement. In this context, a growth medium may be said to not contain any substantial levels of added carbonic anhydrase enzyme if the level of the concentration of carbonic acid in the non-cellular fraction of the carbonic acid-enriched growth medium is at least about 0.1% w/v, preferably at least 0.2% w/v, 0.3% w/v, 0.4% w/v, 0.5% w/v, 0.6% w/v, 0.7% w/v, 0.8% w/v, 0.9% w/v, 1.0% w/v, 1.5% w/v, 2.0% w/v, 2.5% w/v, 3.0% w/v, 4.0% w/v, 5.0% w/v, 6.0% w/v, 7.0% w/v, 8.0% w/v, 9.0% w/v or more such as up to about 10.0% w/v, as described above, and preferably that level can be maintained at a steady level as described above.

In one embodiment, the culture medium of the first aspect of the present invention may be maintained at a pH of less than 7.0, for example from about pH 3.5, 3.75, 4.0, 4.25 or 4.5 to about pH 6.5, from about pH 4.5 to about pH 5.5, or up to about pH 6.4. In this context, the term "about" can optionally refer to ±0.5, 0.4, 0.3, 0.2, 0.1 or less than 0.1 pH units.

The process of enrichment of a culture medium with carbonic acid may be monitored, for example, by monitoring the pH of the medium. As carbonic acid forms and enriches the medium, then the pH of the medium is typically lowered (unless the medium also contains a buffer that resists a pH shift). Thus, in an non-buffered (or weakly buffered) medium, the process of enrichment of the culture medium with carbonic acid may cause a pH drop of, or greater than, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 or more pH units.

Preferably the photosynthetic cell suspension culture is maintained under conditions such that at least 20%, 30%, 40%, 50%, 60%, 70%, 80%, 90% or substantially 100% of the photosynthetic product is produced by photosynthetic cell suspension culture is obtained from the enzymatic conversion of aqueous carbonic acid to the photosynthetic product (for example, as determined by measuring the efficiency of energy conversion of light to product.)

The method of the first aspect of the invention has been found to be surprisingly highly energy efficient in the amount of energy (in particular, light energy) that is required to produce photosynthetic product.

In thermodynamics, it is common to evaluate energy efficiency by looking at reactants and products and using heats of formation. In some cases, people have used heats of combustion as well. There are several major pitfalls to using this approach to liquid photosynthesis. As shown below, a major stumbling block in all such energy equations relates to carefully classifying the reactants and products. In classical photosynthesis of higher plants, the general accepted equation is:

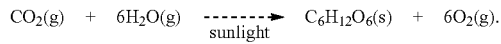

Reaction 1

In this reaction, the reactants are gases and the intended product is solid sugar (glucose).

The applicant has surprising found that this is not the reaction that occurs in photobioreactor when employing a method according to the first aspect of the invention. The applicant has unexpectedly determined that, when carbon dioxide gas enters the cell culture at very high concentrations (not the levels of just 0.036% found in air, but much higher levels such 40% total, i.e. around 1000-fold higher than atmospheric levels), and under appropriate conditions as detailed above, then it is converted to carbonic acid in the medium. If carbonic acid is accumulated in the medium to a level that allows its use by the cells in photosynthesis, then the reaction that occurs in photobioreactor is:

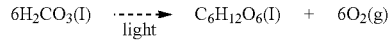

Reaction 2

Thus, in the reaction occurring the method according to the first aspect of the present application, solid sugar is not made, rather sugars and starches are in solution and remain in solution.

Applicant has calculated that, by using the heats of formation for carbonic acid and glucose keeping the sugars in solution and deriving the carbonic acid, the Gibbs Free Energy required for the new process is approximately 65.98 KJ/mol. This is substantially lower than the outdoor crop photosynthesis reaction kinetics given the formation of liquid carbonic acid, and is also lower than the photosynthesis reaction kinetics for the use of gaseous $CO_2$ as a carbon source in a photobioreactor. Thermal energy in this case helps to drive the reaction kinetics forward so some of the wasted absorbed heat is converted into energy used for accelerate the conversion of carbonic acid into sugars.

Accordingly, in a preferred embodiment, the method of the first aspect of the present invention is substantially more energy efficient than photosynthetic processes that do not use aqueous carbonic acid (at all, substantially, or predominantly) as a carbon source for photosynthesis. The amount of light energy (such as number of photons) required to enable the photosynthetic plant or algal cell suspension culture to photosynthetically produce 100 g of the photosynthetic product by the method according to the first aspect of the present invention is preferably 50%, or less, such as less than 40%, less than 30%, less than 20%, less than 10%, less than 9, 8, 7, 6, or 5% than the amount of light energy (such as number of photons) required to enable the same photosynthetic plant or algal cell suspension culture to photosynthetically produce 100 g of the photosynthetic product when supplied with an equivalent volume and rate of atmospheric levels of gaseous carbon dioxide (i.e. approximately 0.036-0.04% $CO_2$), preferably when compared with systems using the same bubble sizes, path lengths, pressures, pH levels and temperatures.

In a preferred embodiment, the culture is maintained in the presence of light consisting, or consisting essentially of (i.e. at least 50, 60%, 70%, 80%, 90%, 95%, 96%, 97%, 98% or 99%), light at photosynthetically active radiation wavelengths, preferably 450-750 nm, more preferably from about 600 to about 700 nm, optionally about 650 nm or 652 nm.

A second aspect of the present invention is based on the applicant's surprising observation that reduced pH in a photosynthetic plant or algal cell suspension culture medium can be used to reduce the energy requirement for photosynthesis. The applicant has found that, by modifying the culture pH, the same quantity of water can be split into hydrogen and oxygen utilising a much lower amount of electrical/light energy, thereby reducing operating costs without reducing output. There is no indication of this in the art, which to the applicant's knowledge, teaches only that a higher incident radiation level is required to increase the output.

Accordingly, the second aspect of the present invention provides a method of producing a photosynthetic product, such as sugar (typically mono- and/or di-saccharides, for example glucose, sucrose, and/or fructose), glyceraldehyde and/or glycerose, comprising maintaining a photosynthetic plant or algal cell suspension culture, in the presence of water, light and carbon dioxide (or instead of carbon dioxide, carbonic acid as described above by the first aspect of the invention), wherein the culture is maintained at a pH of less than about 7.0, preferably about 4.5 to about 5.5. In this context, the term "about" can optionally refer to ±0.5, 0.4, 0.3, 0.2, 0.1 or less than 0.1 pH units.

To put it another way, the second aspect of the present invention provides for the use of a culture medium that is maintained at a pH of less than about 7.0, preferably about 4.5 to about 5.5. The use may be for producing a photosynthetic product, such as sugar (typically mono- and/or di-saccharides, for example glucose, sucrose, and/or fructose), glyceraldehyde and/or glycerose, by maintaining a photosynthetic plant or algal cell suspension culture, in the presence of water, light and carbon dioxide (or instead of carbon dioxide, carbonic acid as described above by the first aspect of the invention), The use is intended to reduce the energy requirement (in particular, the light energy requirement) for photosynthesis and/or production of a photosynthetic product.

Accordingly, the photosynthetic culture of the second aspect of the present invention undergoes photosynthesis and thereby produces a photosynthetic product.

The culture of the first and/or second aspect of the present invention may be maintained in the presence of continuous light. Alternatively, although less preferably, the light may be provided periodically, interspersed with darkness, such as to conform with typical night and day photoperiodicity.

Preferably, the culture of the first and/or second aspect of the present invention is maintained in the presence of light consisting, or consisting essentially (as described above), of light at photosynthetically active radiation wavelengths, preferably 450-750 nm, more preferably about 650 nm.

Preferably, the amount of light energy (such as number of photons) required to enable the photosynthetic plant or algal cell suspension culture of the second aspect of the present invention to photosynthetically produce 100 g of the photosynthetic product is 50%, or less, than the amount of light energy (such as number of photons) required to enable the same photosynthetic plant or algal cell suspension culture to photosynthetically produce 100 g of the photosynthetic product when maintained at a physiological pH of 6.8-7.5, more preferably 7.3.

In one embodiment according to the second aspect of the present invention, the pH of the photosynthetic plant or algal cell suspension culture is maintained at the selected pH using a buffering system, preferably wherein the buffer comprises citric acid and disodium hydrogen orthophosphate or any other suitable buffering system known in the art that is physiologically acceptable to the plant or algal cells in culture. In another embodiment carbonic acid is used to maintain the desired culture pH.

Preferably, the photosynthetic cell suspension culture used in the method of the first and/or second aspect of the invention is a photosynthetic plant cell suspension culture. Although the use of a photosynthetic algal cell suspension culture is also envisaged, this is not the preferred embodiment and so, in one embodiment, the photosynthetic cell suspension culture used in the method of the first and/or second aspect of the invention is not an algal photosynthetic cell suspension culture and/or more particularly is not microalgae, such as described in JP 07-087958 or microalga belonging to the genus *Coccomyxa* as described in JP 11-276157. Thus, any reference to a plant or plant cell in the present application may preferably be construed to include the meaning that it is a non-micoalgal and/or non-algal organism or cell.

Plant and algal cells can be readily distinguished. For example, algae only possess photosystem II; plants have photosystems I and II, and sometimes photosystem III also.

In one embodiment of the first and/or second aspect of the invention, the photosynthetic plant cells for use in a photosynthetic plant cell suspension culture may, or may not, be differentiated photosynthetic plant cells. The differentiated plant cell may be a cell that is specialised for photosynthesis, such as a cell from the leaf or green tissue of a plant, including palisade, leaf mesoderm or petiole cells. Palisade cells may be particularly preferred.

Photosynthetic plant cells may possess one of more characteristics selected from—
(i) as a mean average over 100 randomly sampled cells from the first cell suspension culture, the photosynthetic plant cells contain at least 10, 15, 30, 40, 50 or more chloroplasts per cell;
(ii) a higher chlorophyll content (preferably 2-, 3-, 4-, 5-, 10-, 20-fold or more) than cells of a mesoderm cell suspension culture derived from the same plant species, for example as determined by a spectrophotometric assay which compares the absorbance of a test sample at a wavelength 594 nm (which indicates chlorophyll content) to the absorbance of the same sample at a wavelength of about 1500 nm (which indicates cell density) such that chlorophyll content can be represented by the ratio of $Abs_{594}$:$Abs_{1500}$;
(iii) the ability to produce at least 30, 40, 50 or more g/L of sugar (such as glucose, sucrose and/or fructose) when maintained in cell suspension culture for a week at 20-24° C., under atmospheric pressure, in the presence of excess carbon dioxide, and with exposure to full spectrum light, with intensity at 594 nm of $15.12_{\times 10}^{-3}$ Watts; and/or
(iv) the ability to capture at least 50, 75, 100 mg or more of carbon, per 100 g dry weight cells, per hour, when maintained in cell suspension culture at 20-24° C., under atmospheric pressure, in the presence of excess carbon dioxide, and with exposure to full spectrum light, with intensity at 594 nm of $15.12_{\times 10}^{-3}$ Watts.

In one preferred embodiment, photosynthetic plant cells may, for example, be isolated from a copper-tolerant plant, such as from *Agrostis tenuis*.

In another embodiment, the plant or algal cells used in the photosynthetic cell suspension culture of the first and/or second aspect of the present invention are not genetically modified. In other words, they may preferably (although not necessarily do) not contain any recombinant nucleic acid sequences. Thus, in a preferred embodiment, the plant or algal cells for use in the first and/or second aspect of the present invention may be wild-type. In another embodiment, the plant or algal cells used in the photosynthetic cell suspension culture of the first and/or second aspect of the present invention may not be genetically modified with genes for fatty acid synthase, for butanol biosynthesis, and/or for sugar production, or any other form of genetic modification described in US 2009/0155864.

In one embodiment of the first and/or second aspect of the invention, the method includes the step further of extracting or recovering the photosynthetic product from the photosynthetic plant or algal cell suspension culture medium, preferably by removing the product continuously or on a regular basis from the cell culture medium, for example by filtration, centrifugation, or fractionation. Consequently, the photosynthetic product may be obtained in a more pure or useful form that is substantially separate from the photosynthetic cells, such as a syrup, crystals, or solution (including the simple partitioning the cell suspension culture medium containing the produced photosynthetic product from the photosynthetic cells). In fact, recovery of a cell suspension culture medium containing the produced photosynthetic product from the photosynthetic cells (e.g. by simple partitioning) may be a particularly preferred product, since it maintains the photosynthetic product in solution and can be delivered to other (second) cultures as a growth medium that is enriched in the photosynthetic product, whereupon the second cultures may use the photosynthetic product as, for example, a substrate for their own growth and/or productivity.

By continuously removing the photosynthetic product from the cell culture medium is included the meaning that the photosynthetic product may be removed from the cell culture without any, or any substantial, disruption of the growth of the cell culture which may, for example, be adjudged by monitoring the level of photosynthetic activity as indicated by carbon dioxide and/or carbonic acid consumption or the production of the photosynthetic product, wherein the level of photosynthetic activity during collection of the photosynthetic product should not drop to less than 50%, 60%, 70%, 80%, 90%, 95%, 99% or substantially 100% of the level observed before product collection, over a period of, for example, 30 minutes, 1 hour, 2 hours, 4 hours, 8 hours, 12 hours or 24 hours during which period the photosynthetic product is removed. Suitable techniques that enable for continuous removal of the photosynthetic product are known in the art and include, for example, dialysis of the culture medium.

In one embodiment, the step of extracting the photosynthetic product has the effect of preventing the level of the photosynthetic product accumulating to a level that inhibits the production of further photosynthetic product, preferably such that the level of the photosynthetic product is prevented from accumulating above the level of 600 g/L, 500 g/L, 400 g/L, 300 g/L, 200 g/L, 100 g/L, 50 g/L or less.

Preferably the volume of the culture medium used in the first and/or second aspect of the present invention is at least 10,000 L, such as 20,000 L, 30,000 L, 40,000 L, 50,000 L, or more The method of the first and/or second aspect of the present invention may be used to produce sugars in a method employing two-cell culture system, in place of the "first cell suspension culture of photosynthetic plant cells" as described in any of claims 33-88 of WO 2009/133351; which claims and related disclosure thereof in the description are specifically incorporated herein by reference.

Accordingly, the present invention also provides a method for the production of a biological product, the method comprising
  (i) maintaining a first cell suspension culture of photosynthetic plant or algal cells in accordance with a method as defined by the first or second aspects of the invention, as described above, under conditions that allow the cultured cells to photosynthesize and thereby generate and release photosynthetic product (such as sugars, typically mono- and/or di-saccharides (for example glucose, sucrose, and/or fructose)) into the surrounding culture medium; and
  (ii) maintaining a second cell culture in the presence of the photosynthetic product generated by the first cell suspension culture to allow growth of the second culture and the production of a biological product.

Optionally the method further comprises the step of extracting the biological product from the second cell culture, and further optionally comprises further purifying and/or processing (including chemically modifying and/or formulating with one or more additional substances or components) the thus-extracted biological product. The nature of the extraction step will depend on the nature of the biological product and can be readily determined by the skilled person. Where the biological product produced by the second cell culture is at least one fatty acid and/or oil produced by a plant cell culture, then it may be extracted from the second cell culture by any suitable technique, such as any of the continuous or non-continuous processes discussed in WO 2009/133351, the contents of which are incorporated herein by reference. The nature of any purification and/or processing steps for further purifying and/or processing the thus-extracted biological product will depend on the nature of the biological product and can be readily determined by the skilled person.

Any cells may be cultured in the second cell culture. Typically, the cells may be prokaryotic or eukaryotic, such as bacterial, fungal, plant, animal or human cells. It may be preferred that the second cell culture is a cell suspension culture of oil-producing plant cells, such as a culture that is described as the first aspect of the invention in WO 2009/133351, the contents of which are incorporated herein by reference. Alternatively, for example, the second cell culture may be a culture of microorganisms, such as bacteria or fungi, including yeast. Exemplary yeast include *Saccharomyces* species. In one embodiment, the second cell culture may be a cell culture for making ethanol or other equivalent biofuel (e.g. another alcohol) and thus the cells in the cell culture may be a microorganism, such as yeast, that can convert sugar into the ethanol or other equivalent biofuel. Thus, the cells of the second cell culture may be microorganisms, such as yeast (for example, a *Saccharomyces* species), and the biological product may be an alcohol, such as ethanol.

The biological product may be the cells of the second cell culture, e.g. it may be biomass. Alternatively, the biological product may be synthesised by the cells of the second cell culture. Biological products synthesised by the second cell culture include at least one fatty acid and/or oil, a proteinaceous product (including recombinantly-encoded proteinaceous products) and/or a metabolite, such as ethanol.

In one embodiment, the cells of the first cell suspension culture and the cells of the second cell culture may be in fluid communication with each other. Thus, for example, they may be mixed together and cultured in the same medium and in the same vessel. Alternatively, the cells of the first cell suspension culture and the cells of the second cell culture may be held in separate culture vessels, but those separate culture vessels may be connected in fluid communication with each other, so that photosynthetic product (such as sugars) produced by the first (photosynthetic) cell suspension culture can be used by the cells of the second cell culture. This may be achieved, for example, with a 2 tank system, optionally with a filter between the tanks to prevent cross contamination of the cell lines. In other words, the fluid communication between the cells of the first cell suspension culture and the cells of the second cell culture may allow the photosynthetic product released by the cells of the first cell suspension culture to be used as a carbon source by the cells of the second cell culture.

In another embodiment, the cells of the first cell suspension culture and the cells of the second cell culture are each grown in separate culture vessels that are not in fluid communication with each other. In that case, the photosynthetic product (e.g. sugar) released by the cells of the first cell suspension culture may be collected and then fed to the cells of the second cell culture for use as a carbon source. Thus, the method of the second aspect of the present invention may comprise the step of extracting photosynthetic product from the culture medium of the first cell suspension culture and the further step of feeding the extracted photosynthetic product into the second cell culture. Photosynthetic product, such as sugar, may be extracted from the culture medium of the first cell suspension culture by any suitable means, such as by dialysis, molecular filtration, crystallisation and the like. The extract may itself be the culture medium that has been used for the culture of the first cell suspension culture (and thus enriched in sugars or other photosynthetic product from the photosynthetic activity of the cells of the first cell suspension culture) from which the cells of the first cell suspension culture have been removed (e.g. by partition or filtration or by temporary ceasing mixing within the culture to allow the cells of the first culture to settle to the bottom of the culture tank and then removing at least a portion of the photosynthetic product containing growth medium from the tank), wherein the extracted photosynthetic product-enriched media is used directly as the media for the second cell culture. After depletion of the photosynthetic product (such as sugars) from extracted sugar-enriched media occurs, as a consequence of growing the cells of the second cell culture in it, the cells of the second cell culture may be removed from the depleted media (e.g. by partition, filtration or temporary ceasing mixing) and the thus-produced cell-free depleted media may be returned for use as the culture medium of the first cell suspension culture so it can be regenerated (i.e. enriched with sugars and/or other photosynthetic product from the photosynthetic activity of the cells of the first cell suspension culture) again.

Thus, sugar or other photosynthetic product may be extracted from the culture medium of the first cell suspension culture by continuously removing sugar or other photosynthetic product from the cell culture medium of the first cell culture. In other words, sugar or other photosynthetic product may be removed from the cell culture medium of the first cell culture (i) without any, or any substantial, increase in the rate of cell death in the cells of the first cell culture compared to the rate observed during normal culture conditions; and/or (ii) without any, or any substantial, disruption of the growth of the first cell culture which may, for example, be adjudged by monitoring the level of photosynthetic activity as indicated by $CO_2$ consumption and/or sugar or other photosynthetic product production, wherein the level of photosynthetic activity during collection of the sugar or other photosynthetic product should not drop to less than 50%, 60%, 70%, 80%, 90%, 95%, 99% or substantially 100% of the level observed before sugar collection. Suitable techniques that enable for continuous removal of sugar or other photosynthetic product are known in the art and include, for example, dialysis of the culture medium, partition of the cells from at least a portion of the cell culture medium, filtration to separate the cells from at least a portion of the cell culture medium, or by temporary ceasing mixing within the culture to allow the cells of the first culture to settle to the bottom of the culture tank and then removing at least a portion of the growth medium from the tank).

Accordingly the present invention also provides a plant or algal cell suspension culture growth medium, optionally free or substantially free of photosynthetic plant and/or algal cells, that is enriched both in carbonic acid and in photosynthetic product such as sugar, and the use of this growth medium to support the growth of a second cell culture as defined above.

The second cell culture may, for example, be maintained in the presence of sugar or other photosynthetic product generated by the first cell suspension culture at a concentration of the sugar or other photosynthetic product in the range of 20 g/L to 400 g/L, such as up to 300 g/L, 200 g/L, 100 g/L, preferably at the concentration of about 50 g/L.

In one embodiment, the method may comprise maintaining a second cell suspension culture of oil-producing plant cells in the presence of the sugar or other photosynthetic product generated by the first cell suspension culture and under conditions such that the cultured oil-producing plant cells produce at least one fatty acid and/or oil, and optionally further comprising the step of extracting at least one fatty acid and/or oil from the second cell culture, and further optionally purifying and/or processing the thus-extracted at least one fatty acid and/or oil. For example, the at least one fatty acid and/or oil that is extracted is then further processed to convert it to a biofuel (such as FAME), or is optionally further purified and/or used in a downstream process such as by incorporation into a food product, cosmetic, or lubricant.

Accordingly, the steps of maintaining a second cell suspension culture of oil-producing plant cells in the presence of the sugar or other photosynthetic product generated by the first cell suspension culture and under conditions such that the cultured oil-producing plant cells produce at least one fatty acid and/or oil, and extracting the at least one fatty acid and/or oil from the second cell suspension culture of oil-producing plant cells, may be performed in accordance with the method of any one of claims 1 to 23 of WO 2009/133351, the contents of which are specifically incorporated herein by reference, and so preferably a second cell suspension culture of oil-producing plant cells may be maintained at a pH less than about pH 7.0, 6.5, 6.0 or 5.5, such as from about, or greater than, pH 3.0 to about, or less than, 6.5, preferably from about, or greater than, pH 3.5 to about, or less than, 5.5, more preferably from about, or greater than, pH 4.5 to about, or less than, 5.5, such that the cultured cells of the second cell suspension culture of oil-producing plant cells synthesise and secrete at least one fatty acid and/or oil into the cell suspension culture medium.

An oil-producing plant cell present in the second cell suspension culture may be a differentiated plant cell, such as a cell that is specialised in the production and storage of oils, for example a mesoderm cell.

Where the cell suspension culture of photosynthetic plant or algal cells according to the first and/or second aspects of the present invention is fed carbon dioxide from a carbon dioxide source selected from liquid carbon dioxide or gaseous carbon dioxide and/or is fed carbonic acid by a step comprising feeding the photosynthetic plant cell suspension culture with a carbonic acid solution, a solid or liquid precursor thereof, or a gaseous mixture carbon dioxide and one or more other gases, then optionally the liquid or gaseous carbon dioxide source, the carbonic acid solution, the solid or liquid precursor of the carbonic acid solution, or the gaseous mixture is obtained as a by-product of a carbon dioxide-producing process, such as a process of power generation that uses carbon fuels, or a process of biofuel (such as bioethanol or other alcohol) production by microorganisms (such as yeast) that releases carbon dioxide.

Thus, in one optional embodiment, at least the first cell suspension culture of photosynthetic plant or algal cells according to the first and/or second aspects of the present invention, and optionally also a second cell culture as defined above, is or are maintained at the site of the carbon dioxide-producing process, such as at the site of a power generating facility, or at the site of a biofuel (such as bioethanol or other alcohol) generating facility, that generate carbon dioxide as a by-product.

Accordingly, the present invention also provides a two-culture system for producing a biological product, comprising a first cell suspension culture of photosynthetic plant or algal cells according to the first and/or second aspects of the present invention, and a second cell culture, as defined above. The two-culture system may further comprises a carbon dioxide-generating source, and wherein the thus-generated carbon dioxide is fed into the first cell suspension culture and/or used to produce carbonic acid solution, a solid or liquid precursor of a carbonic acid solution, or a gaseous mixture of carbon dioxide and one or more other gases, which is fed into the first cell suspension culture.

In a preferred embodiment, the two-culture system produces at least one fatty acid and/or oil, and thus comprises a second plant cell suspension culture of oil-producing plant cells as defined above.

The present invention also provides a carbon dioxide capture system comprising at least a first cell suspension culture of photosynthetic plant or algal cells according to the first and/or second aspects of the present invention, and optionally also the second cell culture as defined above. Thus, the present invention also provides for the use a first cell suspension culture of photosynthetic plant or algal cells according to the first and/or second aspects of the present invention as a carbon dioxide capture system.

The carbon dioxide capture system may comprise a carbon dioxide-generating source, and wherein the thus-generated carbon dioxide is fed into the first plant cell suspension culture and/or is used to produce carbonic acid solution, a solid or liquid precursor of a carbonic acid solution, or a gaseous mixture carbon dioxide and one or more other gases, which is fed into the first cell suspension culture.

The carbon dioxide capture system may optionally comprises a second cell culture as defined above, such as a plant cell suspension culture of oil-producing plant cells as defined above.

The present invention thus provides for the use of the two-culture system, or of the carbon dioxide capture system, to capture carbon dioxide or a by-product thereof such a carbonic acid solution, or a solid or liquid precursor of a carbonic acid solution. Typically, the carbon dioxide or by-product thereof that is captured is the by-product of a carbon dioxide-producing process, such as a process of power (e.g. electricity) generation that uses carbon fuels, or a process of biofuel (such as bioethanol or other alcohol) production by microorganisms (such as yeast) that releases carbon dioxide. This use may take place at the site of the carbon dioxide-producing process, such as at the site of a power (e.g. electricity) generating facility, or at the site of a biofuel (such as bioethanol or other alcohol) generating facility or other commercial, industrial or natural process, that generates carbon dioxide as a by-product.

Accordingly, the present invention also provides a power (e.g. electricity) generating facility which produces carbon dioxide or a by-product thereof, the facility comprising the two-culture system as defined above, or the carbon dioxide capture system as defined above. In one embodiment, the two-culture system or the carbon dioxide capture system may produce at least one fatty acid and/or oil from the captured carbon dioxide or by-product thereof and, optionally, the thus produced at least one fatty acid and/or oil may be used directly, or indirectly (e.g. by first converting to biofuel) to supplement the fuel used by the power generating facility.

The present invention also provide a generating facility for producing a producing biofuel (such as bioethanol or other alcohol) comprising the two-culture system as defined above, or the carbon dioxide capture system as defined above. Sugars produced by the first cell suspension culture of photosynthetic cells present within the two-culture system or the carbon dioxide capture system may be used to supplement the growth of microorganisms (such as yeast) used in the production of biofuel by the biofuel generating facility.

The present invention also provides an extract of a biological product obtainable by the method described above, such as an extract of at least one fatty acid and/or oil obtainable by a method as described above. The present invention also provides a biofuel obtainable by the processing of the extract of at least one fatty acid and/or oil obtainable by a method as described above.

The present invention also provides for the use of an extract of a biological product obtainable by the method described above, or a biofuel obtainable by the processing of the extract of at least one fatty acid and/or oil obtainable by a method as described above, as a supplementary source of fuel for a carbon dioxide-producing process.

The present invention also provides a photosynthetic plant or algal cell suspension culture, comprising photosynthetic plant or algal cells in a carbonic acid-enriched growth medium as defined above.

The present invention also provides a carbonic acid-enriched growth medium as defined by, and/or suitable for use in a method of, the first aspect of the invention as defined above. The present invention also provides for the use of the carbonic acid-enriched growth medium of the present invention for producing a photosynthetic product by a method as defined above. The present invention also provides for the use of the carbonic acid-enriched growth medium of the present invention for reducing the energetic requirement, for example the light energy requirement, for producing a photosynthetic product with a photosynthetic plant or algal cell suspension culture, compared to the energetic requirement under the same conditions when using an equivalent growth medium that differs only in having and/or maintaining throughout the growth period a lower carbonic acid level, preferably less then 2.0% w/v, 1.5% w/v, 1.0% w/v, 0.9% w/v, 0.8% w/v, 0.7% w/v, 0.6% w/v, 0.5% w/v, 0.4% w/v, 0.3% w/v, 0.2% w/v, 0.1% w/v, 0.05% w/v, 0.02 w/v, 0.01% w/v, 0.001% w/v, 0.0001% w/v or substantially 0% w/v.

The present invention also provides for the use of carbonic acid as a direct substrate for photosynthesis by a photosynthetic plant or algal cell suspension culture.

In addition to the subject matter as defined by the present claims and the foregoing description, the present invention also provides aspects according to the following numbered paragraphs—

Para 1. A method of producing a photosynthetic product, such as sugar (typically mono- and/or di-saccharides, for example glucose, sucrose, and/or fructose), glyceraldehyde, glycerose, and/or one or more starches, comprising maintaining a photosynthetic plant or algal cell suspension culture, in the presence of water, light and carbonic acid, wherein the carbonic acid is provided by feeding the photosynthetic plant cell suspension culture with a carbonic acid solution, a solid or liquid precursor thereof, or a gaseous mixture of atmospheric air and carbon dioxide.

Para 2. The method of paragraph 1 wherein the carbonic acid is provided by feeding the photosynthetic plant or algal cell suspension culture with a gaseous mixture of atmospheric air and carbon dioxide having a carbon dioxide concentration of about greater than 10%, more particularly at, about, or greater than 15%, 20%, 35%, 30%, 35% or 40%, such as about 40%, for example up to about 50%, 45% or 40%.

Para 3. The method of paragraph 2 wherein the carbon dioxide concentration is 30-45%, 35-45%, yet more particularly 40%±4, 3, 2 or 1%, most particularly 40%.

Para 4. The method of paragraph 1, 2, or 3 wherein the carbonic acid is provided by feeding the photosynthetic plant or algal cell suspension culture with a gaseous mixture of atmospheric air and carbon dioxide and the efficiency of absorption of the carbon dioxide component of the gaseous mixture by the photosynthetic plant or algal cell suspension culture is greater than 40%, particularly greater than 50%, 60%, 70%, or 80%, more particularly about 90%, or about 95%, or more.

Para 5. The method of any of paragraphs 1-4 wherein the culture medium is maintained at a pH of less than 7.0, more particularly 4.5 to 6.5, such as 4.5 to 5.5, or even more particularly up to 6.4.

Para 6. The method of any of paragraphs 1-5 wherein the carbonic acid is provided by feeding a gaseous mixture of atmospheric air and carbon dioxide to the photosynthetic plant or algal cell suspension culture medium, and the photosynthetic plant or algal cell suspension culture is maintained at a pressure of at least, or greater than, 1 atm, such as about $\geq 1$ to 4 atm, $\geq 1$ to 2 atm, particularly about 3 atm.

Para 7. The method of any of paragraphs 1-6 wherein the partial pressure of carbon dioxide is greater than $10^{-8}$, particularly greater than $10^{-7}$, $10^{-6}$, $10^{-5}$, $10^{-4}$, such as within the range of about $10^{-5}$ to about $10^{-4}$.

Para 8. The method of any of paragraphs 1-7 wherein the photosynthetic plant or algal cell suspension culture at least 20%, 30%, 40%, 50%, 60%, 70%, 80%, 90% or substantially 100% of the photosynthetic product that is produced by photosynthetic plant or algal cell suspension culture is obtained from the enzymatic conversion of aqueous carbonic acid to the photosynthetic product.

Para 9. The method of any of paragraphs 1-8 wherein the amount of light energy (such as number of photons) required to enable the photosynthetic plant or algal cell suspension culture to photosynthetically produce 100 g of the photosynthetic product is less than 50%, 40%, 30%, 20%, 10%, 9%, 8%, 7%, 6%, or 5% of the amount of light energy (such as number of photons) required to enable the same photosynthetic plant or algal cell suspension culture to photosynthetically produce 100 g of the photosynthetic product when supplied with an equivalent volume and rate of atmospheric levels of gaseous carbon dioxide.

Para 10. The method of any of paragraphs 1-9 wherein the culture is maintained in the presence of light consisting, or consisting essentially, of light at photosynthetically active radiation wavelengths, particularly 450-750 nm, more particularly about 650 nm.

Para 11. A method for producing a photosynthetic product, such as sugar (typically mono- and/or di-saccharides, for example glucose, sucrose, and/or fructose), glyceraldehyde and/or glycerose, comprising maintaining a photosynthetic plant or algal cell suspension culture, in the presence of water, light and a carbon source selected from carbon dioxide and carbonic acid, wherein the culture is maintained at a pH of less than 7.0, particularly 4.5 to 5.5.

Para 12. The method of paragraph 11 wherein the culture is maintained in the presence of light consisting, or consisting essentially, of light at photosynthetically active radiation wavelengths, particularly 450-750 nm, more particularly about 650 nm.

Para 13. The method of paragraph 11 or 12 wherein the amount of light energy (such as number of photons) required to enable the photosynthetic plant or algal cell suspension culture to photosynthetically produce 100 g of the photosynthetic product is 50%, or less, than the amount of light energy (such as number of photons) required to enable the same photosynthetic plant or algal cell suspension culture to photosynthetically produce 100 g of the photosynthetic product when maintained at a physiological pH of 6.8-7.5, more particularly 7.3.

Para 14. The method of any of paragraphs 11-13 wherein the pH of the photosynthetic plant or algal cell suspension culture is maintained at the selected pH using a buffering system.

Para 15. The method of paragraph 14 where the buffer comprises citric acid and disodium hydrogen orthophosphate, or any other suitable buffering system that is physiologically acceptable to the plant or algal cells in culture.

Para 16. The method of any of paragraphs 11-15 wherein the method includes providing carbonic acid by the method of any of paragraphs 1 to 10.

Para 17. The method of any of paragraphs 1-16 wherein the photosynthetic cell suspension culture is a photosynthetic suspension culture of plant cells and contains no, or substantially no, algal cells.

Para 18. The method of paragraph 17 wherein the photosynthetic plant cell is a differentiated photosynthetic plant cell, such as a cell that is specialised for photosynthesis, for example, a cell from the leaf or green tissue of a plant, including a palisade, leaf mesoderm or petiole cell.

Para 19. The method of paragraph 18 wherein the photosynthetic plant cell suspension culture is a suspension culture of plant palisade cells.

Para 20. The method of any of paragraphs 1-19 comprising the step further of extracting or recovering the photosynthetic product from the photosynthetic plant or algal cell suspension culture medium.

Para 21. The method of paragraph 20 wherein the step further of extracting or recovering the photosynthetic product is a continuous process.

Para 22. The method of paragraph 20 or 21 wherein the extracted or recovered photosynthetic product is provided in the form of a syrup, crystals, or solution.

Para 23. The method of any of paragraphs 20-22 wherein the step of extracting the photosynthetic product prevents the level of the photosynthetic product accumulating in the medium of the photosynthetic plant or algal cell culture to a level that inhibits the production of further photosynthetic product, particularly such that the level of the photosynthetic product is prevented from accumulating above the level of 600 g/L, 500 g/L, 400 g/L, 300 g/L, 200 g/L, 100 g/L, 50 g/L or less.

Para 24. The method of any of paragraphs 1-23 wherein the volume of the photosynthetic plant or algal cell suspension culture is at least 10,000 L, such as 20,000 L, 30,000 L, 40,000 L, 50,000 L, or more Para 25. The method of any of paragraphs 1-24 wherein the method is used to provide a photosynthetic product in place of the use of the first cell suspension culture of photosynthetic plant cells as described in any of claims 33-88 of WO 2009/133351; which claims are specifically incorporated herein by reference.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." Unless otherwise stated, in one embodiment, the word "about" may be construed to mean plus or minus 50%, 40%, 30%, 20%, 10%, 5%, or less than 5%, of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

The invention will be further understood with reference to the following non-limiting figures and experimental examples.

FIG. 1 shows level of sugar in the culture medium of a subculture of photosynthetic cell suspension cultures, as described in section 2.2 and 6.0 of Example 2, grown in light conditions in a growth medium with no detectable levels of carbonic acid (the sole carbon source for photosynthesis was a gaseous mixture of 10% carbon dioxide and 90% air), allowing the culture to grow for 14 weeks, before modifying the conditions to generate carbonic acid levels of 35-40 g/L (i.e. about 3.5 to 4% w/v) in the culture medium (by increasing the concentration of carbon dioxide relative to air to 40% carbon dioxide by volume) and continuing to grow. For both the 10% and 40% $CO_2$ feeds, the mean average diameter bubble size was 0.2 mm, the path length was 1.8 m, and the culture pressure was 3.2 atm.

EXAMPLES

Example 1

A plant cell suspension culture was produced in which an unusually highly concentrated level of carbon dioxide, at 40% by volume, was bubbled, using liquid carbon dioxide from a tank which is piped directly to the reactor for conversion to gas and mixing with air to produce the bubbles. The mean average diameter bubble size was 0.2 mm, the path length was 1.8 m, the culture was maintained under a pressure is 3.2 atm, and the culture pH was 3.75, resulting in a level of carbonic acid of 35-40 g/L (i.e. about 3.5 to 4% w/v).

As discussed above, to the Applicant's knowledge there is no other known or published plant culture which operates at this unusually high carbon dioxide concentration in a buffered media, and no previous reports that would have lead the skilled person to focus on providing carbonic acid in an adequate amount for a plant or algal cell suspension culture to use it as the substrate for photosynthesis, instead of using gaseous carbon dioxide.

As shown below, the use of 40% carbon dioxide bubbles, under conditions suitable to form a carbonic acid-enriched growth medium, drives the reaction kinetics of photosynthesis forward to produce sugars and starches. Important to repeat, this is not at all classical photosynthesis. This is a unique liquid culture reaction system with very unusually high carbon dioxide concentrations under conditions that lead to enrichment of the medium with carbonic acid, wherein we must account for the Gibbs free energy and entropy values.

As a result of this, we are able to reduce the amount of light required to drive photosynthesis, and thereby markedly reduce the energy consumption of the process. The system does not use a white light broad spectrum light process like classical photosynthesis.

A production tank uses 12 LED arrays (+4 arrays of 1,500 W each) which are each rated for 500 watts. Thus, each tank has available electrical power of 12,000 total watts for sugar production, plus the energy derived from the high concentration of carbon dioxide as described below. The LED arrays were chosen at a very select frequency. Sunlight or white light in general contains a broad spectrum of frequencies. Another innovation in the technology package is the select use of 652 nm wavelengths, optimized for the particular plant cell component. In field crops, most of the energy incoming is wasted in the form of heat striking the plant leaves and other energy hits the ground and is absorbed and radiated back into the air. The LED arrays used are mounted both internally and externally to the tanks. In the past, some variations were attempted to utilize natural sunlight by conducting it through mirrors or other optics to enter the first step tank. However, very little increase in overall efficiency was observed in part because the wavelengths of natural sunlight are broad and only enter the tank during daylight hours. The arrays do contribute to the temperature of the tank fluids. The total temperature differential is 9° F. This indicates the overall efficiency of the LEDs is still not 100% and some energy is given up at the LED to glass external interface. In general, for optical energy going across a barrier with a differential in refractive index, in this case air and glass, the energy loss is about 0.4 dB, of which some is reflected back and some heats the glass on the outside of the tank. In any case, the temperature rise is anticipated and reasonable.

This process achieves an overall energy efficiency of about 50%, wherein some goes to waste heat requiring cooling in the building in the summer months. If we were to have used broad spectrum lights and generate excessive amounts of heat, that overall efficiency would plummet. Thus it is not simply that the current process takes advantage of the thermodynamics of concentrated species begin added to the liquid culture but also the fact that the energy input is highly targeted to a wavelength optimized for this particular component of the plant cell culture.

In a 24 hour period, once the tank has achieved optimal cell densities, the rate of sugar production is 1,000 kg/day in a solution that achieves a concentration of 50% sugars and starches. In addition, electrical power is used to move fluids inside the reactor. The duty cycle for the pumps is 100% meaning they are on a total of 24 hours during the day. The hp of these pumps are 0.81 hp. This translates to 1.1 kWatts. The total electrical power required for oil manufacture using the two step process is approximately 2 kWatt-hr per 1 liter of oil. That oil has an energy content of 34,000 BTU/liter. Overall, the net energy efficiency of electrical power and chemical energy from the carbon dioxide concentration to oil is about 50%. The balance is in wasted heat, released oxygen, and cell biomass growth and maintenance.

There are several interesting things to note here. One is that part of the process is taking compressed carbon dioxide or gas under pressure and introducing it into the tank. The gas pressure exceeds the tank head pressure which is roughly 6 feet of head plus the gas backpressure. The tank gauge gas pressure is measured as 10 psi. Thus, some of the energy used in the process must consider the gas blowers or compressors used for the carbon dioxide. It may be for free in terms of gas transfer into the reactor but energy is required to move that gas from the flue stack or carbon dioxide tank into the liquid reactor. All energy required to concentrate and liquefy the carbon dioxide must be accounted for in the energy balance because this energy is returned in step one in the photosynthesis reactions.

At a pH of 7.0, the partial pressure of carbon dioxide in the liquid is only $10^{-8}$ whereas at a pH of 6.4 the partial pressure goes up to $10^{-5}$. By the time the pH hits 5.92, the partial pressure of carbon dioxide has hit $10^{-4}$ or 4 orders of magnitude higher concentration. It is quite evident that gas concentration changes significantly with pH. This brings us to several conclusions as demonstrated in the lab and demonstration scale reactors. That is, the reaction rate kinetics are a function of pH and energy is input into the system from the entering 40% carbon dioxide vapor.

Conclusions:

The rate and direction of a chemical reaction depends on the free energy, entropy, and concentration of the reactants and products as well as the temperature and pH of the system. Chemical reactions progress in the direction of high to low energy. We can estimate the direction of the chemical reaction, as well as the equilibrium concentrations of reactant and product, by examining the energy of the reactants and products.

In nature, the concentration of the $CO_2$ reactant (i.e. maximum $CO_2$ concentration in air) is 0.04% v/v (i.e. 1 liter air contains 0.4 ml carbon dioxide), and so provides 0.0007904 g of $CO_2$ per liter of air (since $CO_2$ has a mass of 1.976 g per liter).

The present example uses the $CO_2$ at 40% volume with air so each liter of air contains 400 ml $CO_2$ and so provides 0.7904 g of $CO_2$ per liter of air.

Accordingly, the present example uses 1,000 times the concentration of carbon dioxide compared to the use of atmospheric air. As all other concentrations can be considered to be constant it is this increase in reactant concentration that lowers the energy required by a calculated 1,000 times.

Reported energy of formation for glucose is +2,826 KJ/mol. We have measured Energy of formation for glyceraldehyde as 65.98 KJ/mol. Reported energy of formation for glyceraldehydes is 59.8 KJ/mol.

The sugar concentration in a leaf is usually 10 mg/g or 1% w/w. In contrast, the sugar concentration obtained by the in the current process is 500 mg/g or 50%.

Therefore, if the energy is proportional to the product concentration/reactant concentration, and we consider carbon dioxide and glucose as the only variables (due to excess water and oxygen in both halves of the reaction) then:

Plant ratio is 1/(molarity of carbon dioxide)=1/1.79636E-05=55,668.02

The ratio achieved by the process of the present example is 50/(molarity of carbon dioxide)=50/0.017964=2,783.40

Therefore, we can calculate the photosynthetic efficiency ratio of a plant versus process of the present example as 55,668.016/2,783.4008=20. In other words, the current process is calculated to require 20 times less energy to produce photosynthetic sugars than the plant.

Two molecules of glyceraldehyde form one molecule of glucose. Therefore in the current process, energy=65.98×2× 20=2,639.2 KJ/mol The difference in the energies in the two systems is due to the fact that energy is released as a compound moves from high concentration to a low concentration. This complies with the laws of thermodynamics.

We can calculate this energy for the sugar production from the information above.

As we know the difference in the energy per mole required to be inputted to make sugars in the plant and in the current process we can calculate the potential chemical energy available from the concentration of the carbon dioxide. This is because free energy also depends on the concentration of reactants and products. This is because the movement of molecules from a more to less concentrated state can perform work.

If we take the difference in energy per mole glucose in plant and current process we get 2,507.24 KJ/mol.

This equates to 13.93 KJ/g glucose.

As we know that 1,000 kg glucose converts to 650 liters of oil (at 100% efficiency) then we can work out the energy provided by the carbon dioxide concentration.

1,000 kg glucose contains 13,929,111 KJ of this energy. This equates to 21,429.4 KJ/liter of oil produced.

As demonstrated by measuring electrical power inputs and oil produced in the experimental system, that rather than traditional photosynthesis, a pseudo photosynthesis process more properly named Photo Mediated Enzymatic Glycogenesis takes place.

This is due to the higher concentrations of carbon dioxide and its presence as carbonic acid in the media. Carbonic acid will react with water to form $HCOO^-$ and $H^+$ ions. Formation of these ions releases energy in the form of heat that can be used to enhance the rate of subsequent reactions. The Rubisco enzymes will be able to attach to the $HCOO^-$ ion and convert it to $C_3H_6O_3$ and oxygen.

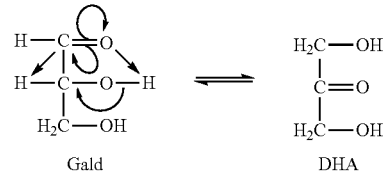

Gald    DHA

As can be seen above, the $C_3H_6O_3$ can exist as two isomers, glyceraldehyde and dihydroxyacetone. It is well reported in literature that these two isomers can combine with the release of energy to form glycerose (a simple aldose sugar) that is the basis of glycerol and fatty acid production.

Total energy provided in the current process:

Light energy=6,000 J/s=518,400,000 J/Day

Moles of sugar produced=1,000,000 gm/(180 gm/mole)=5,555.56 per day

Light energy per mole=93,312 J

Energy from reactants per mole=2,639.2 KJ/mol– (65.98*2)=2,507.24 KJ/mol.

Extra energy from temperature increase above 298° K is not significant as the 6 degree difference in temperatures is only 2% and so gives a contribution of 55.8 KJ/mol glucose.

If the current process is changed so that the final concentration of products is kept to 250 gm/liter of sugars, the energy required is lowered considerably as the contribution from the reactants stays the same but the required energy for the final concentration of products is reduced by half.

Example 2

This example relates to an analysis of the energy balance for rapeseed oil production, by making a photosynthetic product in a first culture tank according to an exemplary method of the present invention and using the photosynthetic product as a carbon source for the growth of a suspension culture of plant cells that produce rapeseed oil in a second culture tank.

Summary

The purpose of this example is to outline the energy balance in an exemplary process. The known energy inputs are compared to the energies that can be potentially released from the process. This example does not seek to provide a full biochemical model for the process; rather it describes the reactions that are known in the process.

Materials and Methods:

1. Induction and Maintenance of Photosynthetic Cell Suspension Culture 1.1 Initiation of Callus Cultures: Preparation of Callus Induction Media Materials: Callus induction media solution; Distilled $H_2O$ to 100%; 3.0% sucrose; 1.0% NAA (naphthalene acetic acid) 0.004% stock solution; 0.44% Murashige and Skoog Basal powdered medium.

Equipment. Glass bottle with cap; Magnetic stirrer; Sterile plastic plant culture dishes; Glass pipettes; pH meter; Autoclave; Laminar flow cabinet; Balance; Nescofilm; Phytagel; 1M NaOH solution; 0.1M NaOH solution.

Callus induction media was prepared using Murashige and Skoog (MS) media obtained from Sigma, with 3% sucrose and 1% naphthalene acetic acid (from a concentrated stock solution of 0.004% w/v.

The prepared media was pH was adjusted to pH 5.75 and solidified with 0.2% phytagel.

The media was autoclaved for 20 mins at 121° C. and then poured out into sterile plastic plant tissue culture dishes.

1.2 Initiation of Callus Cultures: Sterilisation of Plant Tissue

Reagents: Media prepared previously (section 1.1); *Agrostis tenuis* plant tissue.

Equipment: Sterile glass beakers; Sterile distilled water; Sterile scalpel; Sterile tweezers; 10% bleach solution; 70% ethanol solution; 1M NaOH solution; 0.1M NaOH solution.

Plant tissue of *Agrostis tenuis* was sterilised by immersion in 70% ethanol for 2 minutes, followed by immersion in 10% bleach solution for 10 minutes; then washed three times with sterile (autoclaved) distilled water. The sterile plant tissue was aseptically cut into disk shapes in a sterile laminar flow cabinet. Slices were placed onto the prepared plates containing callus induction media, and plates were sealed with Nescofilm. The plates were placed in the dark at 27° C. and callus formation began to appear after about 1 month.

1.3 Media Preparation for Established Cultures

Reagents: Distilled $H_2O$ to 100%; 3% sucrose; 0.44% Murashige and Skoog Basal powdered medium; 1% NAA (naphthalene acetic acid) 0.004% stock solution; 0.01% Vitamin solution (0.05% pyridoxalhydrochlorid, 0.10% thiamine dichloride and 0.05% g nicotinic acid); 1M NaOH solution; 0.1M NaOH solution.

Equipment: 1 L glass bottle; Magnetic stirrer; 20 250 m conical flasks; 20 sheets of foil approximately 20×20 cm; Glass pipettes; pH meter; Autoclave; Laminar flow cabinet; Balance.

Method: Mix 3% sucrose, 0.44% MS powder, 1% NAA stock and 0.01% vitamin stock and prepare to 100% with distilled $H_2O$. Mix using a magnetic stirrer until all dry components dissolved, then pH adjust with 1M and 0.1M NaOH, to 5.75. Take 20 250 ml conical flasks. To each add 50 ml media and seal neck of flask with foil. Sterilize in autoclave, at 121° C., 103 kPa, for 25 minutes. Immediately following sterilization, place flasks in laminar flow cabinet and allow to cool to ambient temperature.

1.4 Inoculation and Subculture of Established Cultures

Reagents: Friable callus; 70% Ethanol.

Equipment: Laminar flow cabinet; Bunsen burner; Prepared media; 20 sterile sheets of foil approximately 20×20 cm; Several pairs of tweezers or small forceps; Wide spatulas with holes.

Method: Sterilize inside of laminar flow cabinet with 70% ethanol. Sterilize all tweezers and spatulas by dipping in 70% ethanol, then flaming till red hot. Allow to cool inside laminar flow cabinet.

Initial inoculation: Remove foil from prepared media flask. Take sterilized tweezers and remove thumbnail sized pieces of friable callus from the plant tissue. Break up into finely dispersed cells and add to flask. Aim to add approximately 5 g tissue to 50 ml media (10% w/v). Flame the neck of the flask, and cover with a sterile sheet of foil. Place the flask on a shaker at 120 rpm, in a light room heated to 27° C. Leave until a thick, dispersed cell suspension culture can be observed (approximately 2 weeks).

Subculture: Remove foil from prepared media flask. Remove foil from flask containing dispersed cell suspension cultures (produced by initial inoculation, as above). Take wide spatula with holes, sterilize, allow to cool and scoop out the cells. Add these cells to the fresh media. Aim to add approximately 5 g tissue to 50 ml media. Flame the neck of the flask, and cover with a sterile sheet of foil. Place the flask on a shaker at 120 rpm, in a dark room heated to 27° C. After 14 days, use the cell suspension culture for further subcultures.

2.0 Photosynthetic Cell Suspension Culture 2.1 Media Preparation for Cell Suspension Cultures Reagents: Distilled $H_2O$ to 100%; 3% sucrose; 0.44% Murashige and Skoog Basal powdered medium; 1% NAA (naphthalene acetic acid) 0.004% stock solution; 0.01% Vitamin solution (0.05% pyridoxalhydrochlorid, 0.10% thiamine dichloride and 0.05% nicotinic acid); 1M NaOH solution; 0.1M NaOH solution; Compressed Air; Compressed Carbon Dioxide (vapour release).

Method: Mix 3% sucrose, 0.44% MS powder, 1% NAA stock and 0.01% vitamin stock and prepare to 100% with distilled $H_2O$. Mix until all dry components have dissolved, then pH adjust with 1M and 0.1M NaOH, to 5.75. Sterilize media and allow to cool to ambient temperature before use.

2.2 Subculture of Cell Suspension Cultures

Reagents: Friable cells; Media prepared previously (section 1.1).

Method: Take cell suspension culture in the exponential phase of growth. Filter cells from media, and use these cells to inoculate fresh media. Aim to add cells to media at approximately 10% w/v. Agitate the culture vessel at 120 rpm, at 27° C., and in light conditions. In light conditions pass through carbon dioxide and air mixture at a concentration of 10% carbon dioxide by volume, allowing the culture to grow under these conditions for 14 weeks, before increasing the concentration of carbon dioxide relative to air to 40% carbon dioxide by volume and continue to grow. For both the 10% and 40% $CO_2$ feeds, the mean average diameter bubble size was 0.2 mm, the path length was 1.8 m, and the culture pressure was 3.2 atm. There were no detectable levels of carbonic acid in the culture fed with 10% level of $CO_2$, and the $CO_2$ feed caused no significant change in the culture medium pH. The 40% $CO_2$ feed resulted in a carbonic acid level of 35-40 g/L (i.e. about 3.5 to 4% w/v) but higher levels can be achieved and used in the practice of this method, and (as a result of the formation of carbonic acid) the pH of the medium dropped from about 5.5 to 3.7.

For further subcultures, the cells should be used when the culture has reached the logarithmic growth phase. For harvesting of the photosynthetic product, glycerose, the cells should be used when the culture has reached the stationary phase. Glycerose was harvested from the culture fed with 40% $CO_2$ by removal of the glycerose-enriched media from the cells in the cell culture, using chromatography separation.

3.0 Induction and Maintenance of Rapeseed Oil-Producing Cell Suspension Culture 3.1 Initiation of Callus Cultures from *Brassica napus*; Preparation of Callus Induction Media Materials: Callus induction media solution; Distilled $H_2O$ to 100%; 3.0% sucrose; 1.0% NAA (naphthalene acetic acid) 0.004% stock solution; 0.44% Murashige and Skoog Basal powdered medium.

Equipment: Glass bottle with cap; Magnetic stirrer; Sterile plastic plant culture dishes; Glass pipettes; pH meter; Autoclave; Laminar flow cabinet; Balance; Nescofilm; Phytagel; 1M NaOH solution; 0.1M NaOH solution.

Callus induction media was prepared using Murashige and Skoog (MS) media obtained from Sigma, with 3% sucrose and 1% naphthalene acetic acid (from a concentrated stock solution of 0.004% w/v. The prepared media was pH was adjusted to pH 5.75 and solidified with 0.2% phytagel. The media was autoclaved for 20 mins at 121° C. and then poured out into sterile plastic plant tissue culture dishes.

3.2 Initiation of Callus Cultures from *Brassica napus*: Sterilisation of Plant Tissue Reagents: Media prepared previously (section 1.1); *Brassica napus* plant tissue.

Equipment: Sterile glass beakers; Sterile distilled water; Sterile scalpel; Sterile tweezers; 10% bleach solution; 70% ethanol solution; 1M NaOH solution; 0.1M NaOH solution.

Plant tissue of *Brassica napus* was sterilised by immersion in 70% ethanol for 2 minutes, followed by immersion in 10% bleach solution for 10 minutes; then washed three times with sterile (autoclaved) distilled water. The sterile plant tissue was aseptically cut into disk shapes in a sterile laminar flow cabinet. Slices were placed onto the prepared plates containing callus induction media, and plates were sealed with Nescofilm. The plates were placed in the dark at 27° C. and callus formation began to appear after about 1 month.

3.3 Media Preparation for Established Cultures

Reagents: Distilled $H_2O$ to 100%; 3% sucrose; 0.44% Murashige and Skoog Basal powdered medium; 1% NAA (naphthalene acetic acid) 0.004% stock solution; 0.01% Vitamin solution (0.05% pyridoxalhydrochlorid, 0.10% thiamine dichloride and 0.05% g nicotinic acid); 1M NaOH solution; 0.1M NaOH solution.

Equipment: 1 L glass bottle; Magnetic stirrer; 20 250 m conical flasks; 20 sheets of foil approximately 20×20 cm; Glass pipettes; pH meter; Autoclave; Laminar flow cabinet; Balance.

Method: Mix 3% sucrose, 0.44% MS powder, 1% NAA stock and 0.01% vitamin stock and prepare to 100% with distilled $H_2O$. Mix using a magnetic stirrer until all dry components dissolved, then pH adjust with 1M and 0.1M NaOH, to 5.75. Take 20 250 ml conical flasks. To each add 50 ml media and seal neck of flask with foil. Sterilize in autoclave, at 121° C., 103 kPa, for 25 minutes. Immediately following sterilization, place flasks in laminar flow cabinet and allow to cool to ambient temperature.

3.4 Inoculation and Subculture of Established Cultures

Reagents: Friable callus; 70% Ethanol.

Equipment: Laminar flow cabinet; Bunsen burner; Prepared media; 20 sterile sheets of foil approximately 20×20 cm; Several pairs of tweezers or small forceps; Wide spatulas with holes.

Method: Sterilize inside of laminar flow cabinet with 70% ethanol. Sterilize all tweezers and spatulas by dipping in 70% ethanol, then flaming till red hot. Allow to cool inside laminar flow cabinet.

Initial inoculation: Remove foil from prepared media flask. Take sterilized tweezers and remove thumbnail sized pieces of friable callus from the plant tissue produced in section 3.2. Break up into finely dispersed cells and add to flask. Aim to add approximately 5 g tissue to 50 ml media (10% w/v). Flame the neck of the flask, and cover with a sterile sheet of foil. Place the flask on a shaker at 120 rpm, in a dark room heated to 27° C. Leave until a thick, dispersed cell suspension culture can be observed (approximately 2 weeks).

Subculture: Remove foil from prepared media flask. Remove foil from flask containing dispersed cell suspension cultures (produced by initial inoculation, as above). Take wide spatula with holes, sterilize, allow to cool and scoop out the cells. Add these cells to the fresh media. Aim to add approximately 5 g tissue to 50 ml media. Flame the neck of the flask, and cover with a sterile sheet of foil. Place the flask on a shaker at 120 rpm, in a dark room heated to 27° C. After 14 days, use the cell suspension culture for further subcultures.

4.0 Oil-Producing Cell Suspension Culture 4.1 Media Preparation for Cell Suspension Cultures Reagents: Distilled $H_2O$ to 100%; 3% sucrose; 0.44% Murashige and Skoog Basal powdered medium; 1% NAA (naphthalene acetic acid) 0.004% stock solution; 0.01% Vitamin solution (0.05% pyridoxalhydrochloride, 0.10% thiamine dichloride and 0.05% nicotinic acid); 1M NaOH solution; 0.1M NaOH solution; Compressed Air.

Method: Mix 3% sucrose, 0.44% MS powder, 1% NAA stock and 0.01% vitamin stock and prepare to 100% with distilled $H_2O$. Mix until all dry components have dissolved, then pH adjust with 1M and 0.1M NaOH, to 5.75. Sterilize media and allow to cool to ambient temperature before use.

4.2 Subculture of Cell Suspension Cultures

Reagents: Friable cells; Media prepared previously (section 1.1).

Method: Take cell suspension culture from section 3.4 in the exponential phase of growth. Filter cells from media, and use these cells to inoculate fresh media. Aim to add cells to media at approximately 10% w/v. Agitate the culture vessel at 120 rpm, at 27° C., and in dark conditions, with aeration using the compressed air. For further subcultures, the cells should be used when the culture has reached the logarithmic growth phase. Due to the pH of 4.0-5.5 the oil is secreted from the cells and rises to the top of the media where it may be floated off.

5.0 Two-Culture Oil Production System

The sugar produced by the cell culture of photosynthetic cells (section 2.2) secretes naturally into the surrounding media. As the air and carbon dioxide mix is fed into the vessel via diffuser plates located at the bottom of the vessel, this gas flow also provide lift to the cells and so performs a constant mixing function.

Conversely, the culture medium of the oil-producing cell culture (section 4.2) becomes sugar depleted during growth as the sugar in the medium is used by the cells for the production of oil.

Once per day sugar-enriched media is removed from the established culture of photosynthetic cells in carbonic-acid enriched medium (fed with 40% $CO_2$), and the sugar-enriched media is used to feed the cell culture of oil-producing cells, using the following steps—

Step 1. Remove 10% by volume of the sugar-depleted medium from the culture of oil-producing cells, and store the removed sugar-depleted medium for later addition to the cell culture of photosynthetic cells in step 3, below.

Step 2. Turn off the gas (air and carbon dioxide) feed into the cell culture of photosynthetic cells, to allow the cells in culture to settle to the bottom of the culture tank. Extract 10% by volume of the sugar enriched media from the top of the vessel, and add it to the culture of oil-producing cells to enhance the level of sugars available to the cells in the oil-producing cell culture.

Step 3. Feed the sugar-depleted media that is stored in step 1, above, into the sugar producing vessel, so that the photosynthetic cells in the culture replenish it with sugar.

It will be appreciated that other volumes of sugar-enriched culture medium and sugar-depleted medium can be transferred between the cultures of photosynthetic cells and the culture of oil-producing cells, and that the transfer may occur at a greater or lesser frequency than once per day. However, we have found that a transfer of 10% volume every 24 hours provides suitable results.

The rapeseed oil produced by the cells in the oil-producing cell culture is excreted from the cells due to the pH of the culture being maintained in the range of 4.0-5.5. Since the excreted oil has a lower specific gravity than the surrounding medium, and is also immiscible with the medium, it floats to the surface where it forms a layer which is then removed via a pipe located above the level of the interface between the medium and that oil layer.

6.0 Results

The subculture of photosynthetic cell suspension cultures, as described in section 2.2 above was grown in light conditions in a growth medium with no detectable levels of carbonic acid (the sole carbon source for photosynthesis was a mixture of 10% carbon dioxide and 90% air), allowing the culture to grow for 14 weeks, before modifying the conditions to generate carbonic acid levels of 35-40 g/L (i.e. about 3.5 to 4% w/v) in the culture medium (increasing the concentration of carbon dioxide relative to air to 40% carbon dioxide by volume) and continuing to grow.

The level of sugar in the culture medium was determined at the start of each week of culture. The results are shown below in Table 1 and in FIG. 1.

TABLE 1

| Week | $CO_2$ level/ carbonic acid level | Measured sugar level (g/L) |
| --- | --- | --- |
| 0 | 10%/ND | 0 |
| 1 | 10%/ND | 0.19 |
| 2 | 10%/ND | 0.27 |
| 3 | 10%/ND | 0.41 |
| 4 | 10%/ND | 0.47 |
| 5 | 10%/ND | 0.47 |
| 6 | 10%/ND | 2.56 |
| 7 | 10%/ND | 3.14 |
| 8 | 10%/ND | 3.15 |
| 9 | 10%/ND | 6.57 |
| 10 | 10%/ND | 9.54 |
| 11 | 10%/ND | 10.11 |
| 12 | 10%/ND | 10.17 |
| 13 | 10%/ND | 13.94 |
| 14 | 10%/ND | 16.57 |
| 15 | 40%/ 3.5-4% w/v | 53.83 |
| 16 | 40%/ 3.5-4% w/v | 81.71 |
| 17 | 40%/ 3.5-4% w/v | 69.89 |
| [...] | [...] | [...] |
| 21 | 40%/ 3.5-4% w/v | 67.57 |
| 22 | 40%/ 3.5-4% w/v | 67.57 |
| 23 | 40%/ 3.5-4% w/v | 66.97 |
| 24 | 40%/ 3.5-4% w/v | 67.14 |
| 25 | 40%/ 3.5-4% w/v | 67.15 |
| 26 | 40%/ 3.5-4% w/v | 67.05 |
| 27 | 40%/ 3.5-4% w/v | 67.05 |
| 28 | 40%/ 3.5-4% w/v | 71.02 |
| 29 | 40%/ 3.5-4% w/v | 70.75 |
| 30 | 40%/ 3.5-4% w/v | 73.98 |
| 31 | 40%/ 3.5-4% w/v | 73.26 |

ND = Not detectable

The data indicate that, after about 10 weeks, the photosynthetic culture fed on 10% gaseous $CO_2$ as the carbon source is well established and, despite having carbonic acid below detectable levels, thereafter shows relatively stable levels of sugar production during the continued use of the 10% $CO_2$ feed, albeit that there is a gradual increase observable as the culture grows between weeks 10-14.

However, the effect of modifying the conditions to produce a medium with enhanced levels of carbonic acid, at about 3.5-4% w/v, produces an immediate, dramatic and stable increase in sugar production without any increase in the light energy input to the system. This shows that, compared to the use of 10% gaseous $CO_2$ as the sole carbon source for photosynthesis, the energy efficiency with which photosynthesis is able to proceed is approximately or greater than 4-fold higher when the conditions used provide a culture medium with enhanced levels of carbonic acid.

Common Misconceptions:

In farming practice, rapeseed is grown in air and soil. The air contains low amounts of carbon dioxide. Growth rates are governed by a classical photosynthesis reaction which is carbon dioxide, gas, and water, combining with light to form solid (soluble) glucose.

In an exemplary process according to the present invention, we do not grow in air or soil. The formation of sugars and starches is catalytic, in an aqueous media that enables carbon dioxide levels 1,000 times that used in traditional farming. The catalysts used are naturally occurring enzymes, used at unusually high concentrations compared to whole plants with roots and leaves.

The exemplified process does not use any GMO (Genetically Modified Organisms). The oil thus produced can be considered food grade.

Additionally, the exemplified process does not use any solvents for oil extraction. Thus, the mass and energy balance does not include oil recovery costs. An advantageous feature of the process is the ability to harvest oil by floatation without cell destruction, a dramatic difference compared to oil seeds or algae.

In some operations, which further involve conversion of the oil to biodiesel using sodium methoxide, will include the step of drying the oil to remove 1% moisture (water), and this can have a slight impact to the overall energy balance to end-product form, although that is not calculated in this example. Rather, this example assesses the amount of energy required to produce the oil, via an exemplary method according to the present invention, and its potential energy in the form of heat of combustion.

General Principles:

Energy is only ever displaced or changed. The amount of input energy is usually greater than the amount of output energy as there are always slight inefficiencies in any process. Furthermore, the energy of a substance will vary depending upon the state it is in, (i.e. a solid, a gas, a liquid) and when energy is transferred to a different state, there is an energy reaction, e.g. heat.

Input Energy:

We have three energy inputs: light, carbon dioxide and "activation energy". We can measure the energy of each of the inputs into the exemplified system.

We measure the energy input for light by the amount of electricity consumed. In this example, the light used for $CO_2$ conversion to sugars and starches in the chloroplast tank is not a white light broad spectrum light like the sun. Rather the light is from LED arrays which are chosen to be at a select frequency between 600-700 nm (for example, 652 nm may be used), a wavelength optimized for the particular plant cell component in the example, as this is the wavelength that is most efficiently used by chloroplasts. The LED arrays contribute to a temperature rise of the tank fluids by 1-2° C., and can be as high as 6° C., but this is anticipated and reasonable.

Energy is also consumed by preparing concentrated carbon dioxide for use in the exemplified process. We know from published information (e.g. Leskovac et al, 2008, *Indian Journal of Biochemistry & Biophysics*, 45, 157-165) that the energy of the concentration of carbon dioxide is 62 kJ per mole. From our experiments, we have shown that 3.117 Kg of carbon dioxide is required for 1.0 kg of oil. The molecular weight of $CO_2$ is 44 so there are (3117÷44) moles added per kg of oil, which equates to 70.84 moles of $CO_2$ per Kg of oil. The energy input required to supply concentrated carbon dioxide for the product of 1 kg of oil is therefore: 62 kJ×70.84=4,392.13 kJ/kg of oil.

Activation and Transition Energy: A Three Step Process

Reaction 1: Chemical Reaction

Much of the chemical energy is a function of the manner in which the carbon dioxide is added to the media.

In this example, this is performed by passing a stream of carbon dioxide gas into a stream of air which then mixes to form a stream of input gas with a level of carbon dioxide of 40% by volume.

This gas stream is passed into the liquid media via diffusion plates which provide micro bubbles of gas which are quickly absorbed into the liquid media. Note that growing seed crops in soil, the carbon dioxide level in air is only 380 ppm. In contrast, the exemplified process operates in liquid (not air) at 1,000 times the concentration of carbon dioxide in air, and with an enzyme concentration many times that of whole plants in soil which expend energy on roots, seeds and vascular tissues that are not required in the photosynthetic cell suspension culture used in the present invention.

The absorption of the gas into the media means that the carbon dioxide reacts with the water in the media which leads to the production of carbonic acid. We have determined the optimum reaction rate kinetics (i.e. the speed at which the reaction takes place and how complete the reaction will be) for the absorption of the $CO_2$ into the media. Conclusions demonstrated in the lab, and in demonstration scale reactors, also show that the reaction rate kinetics is a function of the pH and the concentration level of $CO_2$.

The equation that describes the first step is:

$$CO_2+H_2O \rightarrow H_2CO_3 \text{(carbonic acid)}$$

Reaction 2: Activation

As the carbon dioxide is absorbed into the media, and turns into carbonic acid, energy ("activation" energy) is given off, in line with the laws of thermodynamics (i.e. energy is released as a compound moves from high concentration to a low concentration).

Carbonic acid is not stable at the temperatures in the tanks and will also react with the enzymes within the cells that are present in the media. As a result the carbonic acid will break down into hydrogen carbonate ($HCO_3^-$) and hydrogen ($H^+$) ions. This reaction can be described as follows:

$$H_2CO_3 \rightarrow H^+ + HCO_3^- \text{(bi-carbonate)}$$

Reaction 3: Transition

The enzymes of the Rubisco pathway can use the carbonate ions ($HCO_3$ or $CO_3$) to produce hydrocarbon units and these hydrocarbon units will be joined together. In humans and plants, the highest activity enzyme, with the highest turnover of any known enzyme, is carbonic anhydrase. It allows carbon dioxide exchange in the lungs at an incredible rate. The plant cells in cell suspension culture used in the present example contain these enzymes and the process is able to take exceptional advantage of the high turnover rate in the catalytic reaction of carbon dioxide to form complex carbohydrates.

The reaction can be described as follows:

$$H^+ + HCO_3^- \rightarrow H_2CO \text{(carbohydrate)} + 2OH^- \text{(hydroxide ion)}$$

Energy is needed for these units to be joined together. This energy is provided by NADPH being broken down to NADP+$H^+$. As the amount of NADPH available in the reaction system is limited to the amount present in the cultures cells, then in order to keep the reaction going forward, NADP must be converted back to NADPH. This happens by using the "spare" hydrogen ions from the breakdown of carbonic acid as described in Reaction 3. It is cyclical.

Overall, the production of glyceraldehyde from $CO_2$, via Reactions 1-3 as defined above, can be described as follows:

$$3H_2CO \rightarrow H_6C_3O_3$$

The process uses up 4 NADPH to NADP for each molecule of glyceraldehyde produced.

As the hydrogen ions are used up the pH would be expected to rise. But we have observed that, in practice, it does not, which must mean that hydrogen ions are continually formed. This is due to the continual supply of carbonic acid (in this example, by the continued supply of $CO_2$), which in turn continues to be broken down into the carbon and hydrogen ions.

Our results show that the amount of hydrogen ions is proportional to the amount of $CO_2$. From that understanding, and knowing the pH measurements, the volume of liquid and the amount of $CO_2$ added to the system, the amount of H' ions present in the system can be calculated. Furthermore, knowing the amount of energy associated with a single hydrogen ion, the amount of energy at any given time in the system can be calculated. Note that this liquid enzymatic catalytic system is a dramatic departure from classical farming.

Calculating the Amount of System Energy:

We have experimentally determined that 3.117 Kg of carbon dioxide is required for the production of 1.0 Kg of oil in the exemplified Two-Culture oil production system as defined above in Section 5.0. We have determined that the amount of oil that is made per minute is 0.415 Kg.

Therefore $(3.117 \times 0.415) = 1.2935$ Kg of $CO_2$ is used per minute by the exemplified system. Since the molecular weight of $CO_2$ is 44, the exemplified system is therefore using $(1293.5 \text{ g} \div 44=)$ 29.39 moles of $CO_2$ per minute.

The amount of energy associated with one $H^+$ is 13.6 electron volts which equals$=2.18 \times 10^{-18}$ joules. In one mole of $H^+$ there therefore are $6.022 \times 10^{23}$ molecules (Avagadro's constant). Therefore, one mole of a hydrogen ions has an energy of $2.18 \times 10^{-18} \times 6.022 \times 10^{23}$ which$=1.31 \times 10^3$ kJ.

Therefore, knowing that the exemplified system uses 29.39 moles of $CO_2$ per minute, and knowing the $CO_2$ forms carbonic acid which then breaks down to form at least one hydrogen ion, there will be $(29.39 \times 1.31 \times 10^3$ kJ$)$ or 38,501 kJ energy associated with the hydrogen ions per minute.

38,501 kJ per minute energy is created which produces 0.415 Kg of oil per minute. The amount of energy therefore within the system to create 1.0 kg of oil is $(38,501 \div 0.415) = 1.55 \times 10^5$ i.e. 155,000 kJ per kg of oil.

Total Input Energy is therefore:

| Energy | Description | Measurement Gauge | Measurement |
| --- | --- | --- | --- |
| Input Energy | The energy associated with the different inputs i.e. light, $CO_2$, and the media:<br>1. Light<br>2. $CO_2$<br>3. Media | 1. Consumption of electricity.<br>2. Accepted published criteria.<br>3. Measured as a function of pH. Measured as a function of pH. | 1. 1,990 kJ/kg<br>2. 4392.136 kJ/kg<br>3. Included in activation energy.<br>155,000 KJ/Kg |
| Activation | The diffusion of the $CO_2$ into the media causes the $CO_2$ to breakdown which releases energy. | | |
| | | TOTAL | 161,382 KJ/Kg |

Release of Oil:

The Rubisco enzymes in the cultured plant cells will be able to attach to the $HCO_3^-$ and convert it to $C_3H_6O_3$ and oxygen. The glyceraldehyde is removed from the first tank and passed into the second tank to act as a carbon course for a cell suspension culture of plant cells that produce and release rapeseed oil.

$C_3H_6O_3$ can exist as two isomers, which are glyceraldehyde and dihydroxyacetone. Literature reports that these two isomers can combine, with the release of energy, to form glycerose (a simple aldose sugar) which is the basis of glycerol and fatty acid production to create oil, which is represented in the following formula:

$$29\ C_3H_6O_3 + 36H^+ \longrightarrow$$

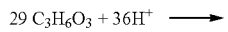  $\longrightarrow C_{57}H_{105}O_9 + 52\ H_2O + 13\ O_2$

Energy Outputs:

The measurable energy outputs of the exemplified system are the potential energy (combustion) of the rapeseed oil, and the heat produced. Similarly to field grown crops, the process also releases oxygen.

Combustion of rapeseed oil is known to be 39.59 MJ/kg or 39,590 kJ/kg.

As a result of the combination of the inputs, there is a temperature rise proportional to the amount and rate of $CO_2$ and air mix. The more $CO_2$ that is added, the higher the temperature rises. Our data shows that there is about a 5° C. rise in the exemplified system. Formation of the hydrogen ions also releases energy in the form of heat. The heat generated is a form of energy that can be used to enhance the rate of subsequent reactions, as the hotter the temperature, the more a molecule vibrates and therefore combines more easily.

The heat evolved from the tank is 13,196 kJ, which is 22.0675 kJ/kg. This is calculated based on the heat capacity of the stainless steel tanks and the temperature rise of 5° C.

Total Energy output is therefore:

| Energy | Description | Measurement Gauge | Measurement |
| --- | --- | --- | --- |
| Oil | The energy in the oil. | Combustion of Oil | 39,590 kJ/kg |
| Heat | Heat | Temperature | 22.06 kJ/kg |
| Cellular | The energy | Very difficult | Negligible % |

-continued

| Energy | Description | Measurement Gauge | Measurement |
| --- | --- | --- | --- |
| Metabolism | used up to maintain the cells | to measure | |
| | | TOTAL | 39,612 kJ/kg |

Energy Balance:

The total energy input is a combination of three factors, light, $CO_2$, and the media. The combination of those elements creates additional significant energy within the system. The output energy is the combustion of oil and heat.

| Input Energy: (KJ/Kg) | | Output Energy: (KJ/Kg) | |
| --- | --- | --- | --- |
| LEDs | 1990 | 39,590 | Combustion of oil |
| Concentration of $CO_2$ | 4392 | 22 | Heat |
| Activation Energy | 155,000 | | |
| Total | 161,382 | → 39,612 | |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of producing a sugar-comprising photosynthetic product, wherein the method comprises maintaining a photosynthetic non-algal plant cell suspension culture, in the presence of water, light and in a carbonic acid-enriched growth medium, wherein the concentration of carbonic acid in the carbonic acid-enriched growth medium is at least about 0.1% w/v.

2. The method of claim 1, wherein the concentration of carbonic acid in the carbonic acid-enriched growth medium is of from about 0.1% w/v to about 10% w/v.

3. The method of claim 1, wherein the level of carbonic acid in the carbonic acid-enriched growth medium is maintained at a steady level.

4. The method of claim 1, wherein the culture medium is maintained at a pH of less than 7.0.

5. The method of claim 1, wherein the culture is maintained in the presence of constant light.

6. The method of claim 1, wherein the photosynthetic non-algal plant cell suspension culture is a suspension culture of differentiated photosynthetic non-algal plant cells.

7. The method of claim 6, wherein the photosynthetic plant cell suspension culture is a suspension culture of plant palisade cells, leaf mesoderm cells or petiole cells.

8. The method of claim 1, wherein the sugar-comprising photosynthetic product is selected from the group consisting of sugar, glyceraldehyde, glycerose, one or more starches, and a combination of any of the preceding.

9. The method of claim 8, wherein the photosynthetic product is a sugar selected from the group consisting of a mono-saccharide, a di-saccharide, glucose, sucrose, fructose, and a combination of any of the preceding.

10. The method of claim 1, further comprising the step of extracting or recovering the sugar-comprising photosynthetic product from the carbonic acid-enriched growth medium.

11. The method of claim 10, wherein the step further of extracting or recovering the photosynthetic product is a continuous process.

12. The method of claim 10, wherein the extracted or recovered photosynthetic product is provided in the form of a syrup, crystals, or solution.

13. The method of claim 1, wherein the photosynthetic non-algal plant cell suspension culture has a volume that is at least 10,000 L.

14. The method of claim 1, further comprising the production of a biological product of a second culture, the method comprising (i) maintaining a first cell suspension culture of photosynthetic non-algal plant cells in accordance with the method as defined by claim 1 such that cells of the photosynthetic non-algal plant cell suspension culture photosynthesize and thereby generate and release sugar-comprising photosynthetic product into the surrounding culture medium; and (ii) maintaining a second cell culture in the presence of the photosynthetic product generated by the first cell suspension culture to allow growth of the second culture and the production of a biological product by the second culture.

15. The method of claim 14, wherein the biological product is biomass.

16. The method of claim 14, wherein the biological product is selected from the group consisting of a fatty acid, oil, a combination of a fatty acid and oil, a proteinaceous product and a metabolite.

17. The method of claim 14, wherein the second cell culture is a culture of prokaryotic cells or eukaryotic cells.

18. The method of claim 14, wherein the second cell culture is a culture of microorganisms.

19. The method of claim 14, wherein the second cell culture is a cell suspension culture of oil-producing plant cells, the method comprising maintaining the second cell suspension culture of oil-producing plant cells in the presence of the photosynthetic product generated by the first cell suspension culture and under conditions such that the cultured oil-producing plant cells produce fatty acid, oil, or a combination of fatty acid and oil.

20. The method of claim 14, further comprising the step of extracting the biological product from the second cell culture.

21. The method of claim 19, further comprising the step of extracting the fatty acid, oil, or combination of fatty acid and oil, from the plant cell culture of oil-producing plant cells.

22. The method of claim 20, further comprising purifying, or processing, or purifying and processing, the extracted biological product.

23. The method of claim 21, wherein the fatty acid, oil, or combination of fatty acid and oil, that is extracted is then further processed to convert it to a biofuel.

24. The method of claim 19, wherein the oil-producing plant cells present in the second cell suspension culture are differentiated plant cells.

25. The method of claim 24, wherein the differentiated plant cells are cells that are specialized in the production and storage of oils.

26. A two-culture system for producing a biological product, comprising a first cell suspension culture and a second cell culture, each as defined by claim 14 wherein the first cell suspension culture is a cell suspension culture of photosynthetic non-algal plant cells that is maintained in the presence of water, light, and in a carbonic acid-enriched growth medium, wherein the concentration of carbonic acid in the carbonic acid-enriched growth medium is at least about 0.1% w/v.

27. A carbon dioxide capture system comprising at least the first plant cell suspension culture as defined by claim 14 wherein the first cell suspension culture is a cell suspension culture of photosynthetic non-algal plant cells that is maintained in the presence of water, light, and in a carbonic acid-enriched growth medium, wherein the concentration of carbonic acid in the carbonic acid-enriched growth medium is at least about 0.1% w/v.

28. A photosynthetic non-algal plant cell suspension culture that is capable of producing a sugar-comprising photosynthetic product when maintained in the presence of water, light and in a carbonic acid-enriched growth medium, wherein the concentration of carbonic acid in the carbonic acid-enriched growth medium is at least about 0.1% w/v.

29. A carbonic acid-enriched growth medium as defined by, or suitable for use in, the method of claim 1, wherein the concentration of carbonic acid in the medium is at least about 0.1% w/v.

30. The method of claim 4, wherein the culture medium is maintained at a pH of about 4.5 to about 6.5, or about 4.5 to about 5.5, or up to about 6.4.

31. The method of claim 6, wherein the plant cell specialized for photosynthesis is a cell from the leaf or green tissue of a plant.

32. The method of claim 13, wherein the photosynthetic non-algal plant cell suspension culture has a volume that of at least 20,000 L, at least 30,000 L, at least 40,000 L, or at least 50,000 L.

33. The method of claim 16, wherein the proteinaceous product is a recombinantly-encoded proteinaceous product and the metabolite is ethanol.

34. The method of claim 17, wherein the cells of the second culture are bacterial cells, fungal cells, plant cells, animal cells or human cells.

35. The method of claim 18, wherein the microorganisms are yeast cells.

36. The method of claim 18, wherein the biological product is an alcohol.

37. The method of claim 19, wherein the photosynthetic product is a sugar.

38. The method of claim 21, wherein the fatty acid, oil, or combination of fatty acid and oil, that is extracted is purified to produce a purified extract.

39. The method of claim 21, wherein the fatty acid, oil, or combination of fatty acid and oil, that is extracted is used in a downstream process.

40. The method of claim 39, wherein the downstream process involves incorporation of the fatty acid, oil, or combination of fatty acid and oil, that is extracted into a product selected from the group consisting of a food product, a cosmetic and a lubricant.

41. The method of claim 21, wherein the fatty acid, oil, or combination of fatty acid and oil that is extracted is further purified to produce a purified extract, and the purified extract is used in a downstream process.

42. The method of claim 41, wherein the downstream process involves incorporation of the purified extract into a product selected from the group consisting of a food product, a cosmetic and a lubricant.

43. The method of claim 25, wherein the cells specialized in the production and storage of oils are mesoderm cells.

44. The method of claim 6, wherein the plant cell specialized for photosynthesis is a palisade, leaf mesoderm or petiole cell.

45. The method of claim 35, wherein the yeast cells are *Saccharomyces* species.

46. The method of claim 36, wherein the alcohol is ethanol.

* * * * *